(12) United States Patent
Wang et al.

(10) Patent No.: US 7,427,689 B2
(45) Date of Patent: Sep. 23, 2008

(54) ERBB-2 SELECTIVE SMALL MOLECULE KINASE INHIBITORS

(75) Inventors: Shaomeng Wang, Saline, MI (US); Dajun Yang, Rockville, MD (US); Istvan Enyedy, Hamden, CT (US)

(73) Assignee: Georgetown University, Washington, DC (US)

( * ) Notice: Subject to any disclaimer, the term of this patent is extended or adjusted under 35 U.S.C. 154(b) by 665 days.

(21) Appl. No.: 10/343,267

(22) PCT Filed: Jul. 30, 2001

(86) PCT No.: PCT/US01/23869

§ 371 (c)(1), (2), (4) Date: Aug. 4, 2003

(87) PCT Pub. No.: WO02/09684

PCT Pub. Date: Feb. 7, 2002

(65) Prior Publication Data

US 2004/0023957 A1 Feb. 5, 2004

Related U.S. Application Data

(60) Provisional application No. 60/221,515, filed on Jul. 28, 2000.

(51) Int. Cl.
C07C 205/00 (2006.01)
(52) U.S. Cl. .................................................. 562/434
(58) Field of Classification Search ................. 514/310; 562/434
See application file for complete search history.

(56) References Cited

U.S. PATENT DOCUMENTS

| | | | |
|---|---|---|---|
| 3,347,885 A | 10/1967 | Jones et al. | 260/412.4 |
| 3,364,242 A | 1/1968 | Johnson et al. | 260/420 |
| 3,551,502 A * | 12/1970 | Seki et al. | 568/584 |
| 3,647,791 A | 3/1972 | Rossi et al. | 260/268 |
| 4,297,341 A | 10/1981 | Waller et al. | 424/80 |
| 4,747,979 A | 5/1988 | Gimber et al. | 260/412.4 |
| 4,806,568 A | 2/1989 | Vander Jagt et al. | 514/522 |
| 5,026,726 A | 6/1991 | Jagt et al. | 514/468 |
| 5,059,717 A | 10/1991 | Ibragimov et al. | 568/438 |
| 5,077,441 A | 12/1991 | Kuk et al. | 568/761 |
| 5,112,637 A | 5/1992 | Hron, Sr. et al. | 426/629 |
| 5,260,327 A | 11/1993 | Kim et al. | 514/405 |
| 5,277,909 A | 1/1994 | Schmidt et al. | 424/195.1 |
| 5,385,936 A | 1/1995 | Flack et al. | 514/548 |
| 5,759,837 A | 6/1998 | Kahajda et al. | 435/193 |
| 5,780,675 A | 7/1998 | Royer et al. | 562/467 |
| 6,114,397 A | 9/2000 | Flack et al. | |
| 6,576,660 B1 | 6/2003 | Liao et al. | 514/456 |
| 6,608,107 B2 | 8/2003 | Wong et al. | 514/548 |
| 6,677,377 B2 * | 1/2004 | Lin et al. | 514/636 |
| 6,703,382 B2 * | 3/2004 | Wang et al. | 514/183 |
| 2002/0137801 A1 | 9/2002 | Wong et al. | |
| 2003/0082101 A1 | 5/2003 | Taylor et al. | |
| 2003/0119894 A1 | 6/2003 | Murthy et al. | |

FOREIGN PATENT DOCUMENTS

| | | |
|---|---|---|
| CH | 676360 A5 | 12/1988 |
| DE | 1 917 341 | 4/1969 |
| EP | 0 651 636 B1 | 7/1993 |
| JP | 01132542 A | 11/1987 |
| SU | 1351915 A1 | 6/1982 |
| WO | WO 02/41828 A2 | 5/2002 |
| WO | WO 02/47673 A2 | 6/2002 |

OTHER PUBLICATIONS

Zhang et al. Bioorg. & Med. Chem. Letters vol. 14, 111-114 (2004).*
Vichkanova et al., Antibiotics (Moscow) 13:828-829 (1968) (Abstract in English).
V. Amberger, et al., Cancer Res., 58:149-158 (1998).
Wick et al. (W. Wick, et al., FEBS Lett., 440:419-424 (1998).
S. Mohanam, et al., Cancer Res. 53:4143-4147 (1993).
P. Pedersen, et al., Cancer Res., 53:5158-5165 (1993).
Nuria Rubio, Lab Invest, 81:725-734 (2001).
Fernández et al., Cell Death Differ., 7:350-359 (2000).
J. Reed, Nature, 387:773-776 (1997).
S. Frisch and E. Ruoslahti, Curr. Opin. Cell Biol., 9:701-706 ((1997).
D. Del Bufalo, et al., FASEB J., 11:947-953 (1997).
Razakantoanina et al. Parasitol. Res., 86:665-668 (2000).
Dao et al. Bioorg. Med. Chem., 11:2001-2006 (2003).

(Continued)

*Primary Examiner*—Michael Hartley
*Assistant Examiner*—Shirley V Gembeh
(74) *Attorney, Agent, or Firm*—Casimir Jones S.C.

(57) ABSTRACT

A novel method for erbB-2 kinase inhibition by compounds identifies through computational modeling and data processing and/or rational and de novo drug design is provided the compounds bind erbB-2 kinase molecules and which can be used as erbB-2 kinase agonists or antagonists. These compounds are useful especially in the treatment of cancer, particularly breast cancer, and can be used alone or in combination with other chemotherapeutic agents, particularly with hercetin, a humanized anti-HER-2 antibody, or with radiation therapy. A specific compound which is exemplified is "compound B17"=methyl-(p-nitrophenyl)-2-propynoate.

3 Claims, 11 Drawing Sheets

OTHER PUBLICATIONS

Deck et al. J. Med. Chem., 34:3301-3305 (1991).
Przybylski et al. J. Mol. Structure, 611(1-3):193-201 (2002).
R.E. Royer et al., J. Med. Chem., 38:2427-2432 (1995).
R.E. Royer et al., Biologically active derivativse of gossypol: synthesis and antimalarial activities of peri-acylated gossylic nitriles:, J. Med. Chem., 29:1799-1801 (1986).
C.M. Venuti, J. Org. Chem., 46(15):3124-3127 (1981).
P.C. Meltzer et al., J. Org. Chem., 50(17):3121-3124 (1985).
R. Adams et al., J. Am. Chem. Soc., 60:2193-2204 (1938).
Le Blanc et al. "An in vitro study of inhibitory activity of gossypol, a cottonseed extract, in human carcinoma cell lines", Pharmacol. Res., 46:551-555 (2002).
Baumgrass et al., "Reversible inhibition of calcineurin by the polyphenolic aldehyde gossypol", J. Biol. Chem., 276:47914-47921 (2001).
Shelley et al., "Structure-activity studies on gossypol in tumor cell lines," Anticancer Drugs, 11:209-216 (2000).
Sonenberg et al., "Anti-fertility and othe ractions of gossypol analogues", Contraception, 37:247-255, (1988).
Whaley et al, ."Monkey lactate dehydrogenase-C4 as a model for the interaction of enzymes with gossypol", Contraception, 33:605-616 (1986).
Dorsett et al., "Letter: Antivrial activity of gossypol and apogossypol", J. Pharm. Sci., 64:1073-1075 (1975).
Wu et al., "Synthesis and antifertility actions of gossypol derivatives and phenol aldehydes", Yao Xue Xue Bao, 24:502-511 (1989).
Hoffer et al., "Antifertility, spermicidal and ultrastructural effects of gossypol and derivatives administered orally and by intratesticular injections", Contraception, 37:301-331 (1988).
Guo et al., "Synthesis of mono-aldehyde gossypol and its analogues", Yao Xue Xue Bao, 22:597-602 (1987).
Manmade et al., "Gossypol. Synthesis and in vitro spermicidal activity of isomeric hemigossypol derivatives", Experientia, 39:1276-1277 (1983).
Dowd, Chirality, 15:486 (2003).
Ciesielska et al., Chem. Phys. Lett. 353:69 (2002).
Vermel et al., Antitumor Activity of Gossypol in Experiments on Transplanted Tumours 39-43 (1963).
Freedman et al., Chirality, 15:196 (2003).
J.C. Reed, Pharmacology, 41:501-553 (1997).
J.C. Reed et al., J. Cell Biochem., 6:23-32 (1996).
Z. Han et al., Cancer Res., 56:621-628 (1996).
S.W. Muchmore et al., Nature, 381:335-341 (1996).
A.M. Petros et al., Protein Sci., 9:2528-2534 (2000).
A.M. Petros et al., Proc. Natl. Acad. Sci. U.S.A., 98:3012-3017 (2001).
X.M. Yin et al., Nature, 369:321-323 (1994).
S.C. Cosulich et al., Curr. Biol., 7:913-920 (1997).
A. Sali et al., Structure, Function, and Genetics, 23:318-326 (1995).
A.Sali, Curr. Opin. Biotech., 6:437-451 (1995).
J.L. Wang et al., Cancer Res., 60:1498-1502 (2000).
J.L. Wang et al., Proc. Natl. Acad. Sci. U.S.A., 97:7124-7129 (2000).
Sattler et al., Science, 275:983-986 (1997).
B.R. Brooks et al., J. Comp. Chem., 4,187-217 (1983).
P.V.R. Schleyer et al., Charmm: The Energy Function and Its Parameterization with an Overview of the Program, in The Encyclopedia of Computational Chemistry, 1:271-277 eds., John Wiley & Sons, Chichester (1998).
S. Makino and I.D. Kuntz, J. Comput. Chem. 18:1812-1825 (1997).
I.J. Enyedy et al., J. Med. Chem., 44:313-4324 (2001).
Leschev, "Influence of the Extract of Eleutherococcus senticosus on development of experimental pituitary adenomas in rats", Institute of Oncology of the U.S.S.R. Academy of Medical Sciences, 60-67 (1966).
Willemsen, An Oxazoline-Based Approach to the Total Asymmetric Synthesis of (S)-Gossypol, UMI PROquest Digial Dissertations—Full Citation & Abstract.
La Blanc et al., An in vitro study of inhibitory activity of gossypol, a cottonseed extract, in human carcinoma cell lines, Pharmacol. Res. 46(6):551-5 (2002).
Griffith et al., Bioenvision Successfully Completes Formulation Research to Develop Gossypol as a Novel Anti-Cancer Agent, Bioenvision News (2003).
Saydachmov et al., Uebekskii Khimicheski Zhumal (1):11-13 (1994).
Zakhidov et al., Modifying Cytogenetic Effects of Gossypol and Derivatives, Library National Institutes of Health (1994).
Yerukhimov, Treatment of Bladder Tumors With Gossipol And Ionol In Combination With Surgical Intervention, Issues in Oncology, XI (1966).
Kuznezova et al., Pharmacol. Toxicol., Boston Library Boston Spa (1979).
Zhong et al., National Library of Medicine, 2:159-161 (1982).
Zhang et al., Inhibitory effects (-)-gossypol on proliferation and keratinocyte growth factor expression in human breast epithelial cells, stromal cells, and adipocytes, American Association fro Cancer Research 38:218 (1997).
Zheng et al., Gossypol (GP) Stimulates Transforming Growth Factor Beta (TGF-β) Gene Expression in Human Breast Cancer Cell Line, The FASEB Journal 10:A757 (1996).
Zheng et al., Studies on the Resolution of Racemic Gossypol, ACTA Pharmaceutica Simica 25(6):430-434 (1990).
Adlakha et al., Inhibition of DNA Polymerase α And Ribonucleotide Reductase by By Gossypol, Proceedings of AACR 26:249:982 (1985).
Akhila et al., Biosynthesis of Gossypol in *Thespesia populnea*, Phytochemistry 33:335-340 (1993).
Badria et al., Antimitotic Activity of Gossypol and Gossypolone, Pharmaceutical Biology, 39:120-126 (2001).
P. Baille et al., Clin. Cancer Res., 3:1535-1538 (1997).
Balci et al., Gossypol induced apoptosis in the human promyelocytic cell line HL60, Cytogenet Cell Genet 85:5-181 (1999).
Balci et al., Gossypol Induced Apoptosis in the Human Promyelocytic Leukemia Cell Line HL 60, Tohoku J. Exp. Med. 189:51-57 (1999).
Band et al., Antiproliferative Effect Of Gossypol and Its Optical Isomers on Human Reproductive Cancer Cell Lines, Gynecologenic Oncology 32:273-277 (1989).
Band et al., Cytocidal Effects of Gossypol and Its Optical Isomers on Reproductive Cancer Cell Lines,Gynecologic Oncology 23:261 (1986).
Benz et al., Lactic Dehydrogenase Isozymes, $^{31}P$ Magnetic Resonance Spectroscopy, and In Vitro Antimitochondrial Tumor Toxicity with Gossypol and Rhodamine-123, J. Clin.Invest. 79:517-523 (1987).
Benz et al., Selective Toxicity of Gossypol Against Epithelial Tumors and its Detection by Magnetic Resonance Spectroscopy, Contraception 37:221-229 (1988).
Benz et al., Gossypol Enantiomers (+, −) Differentially Uncouple Tumor Mitochondria, Block Glutathione-S-Transferase Acitivity, and Inhibit Cellular Proliferation, Proceedings of AACR 29:322 (1988).
Benz et al., Biochemical Correlates of the Antitumor and Antimitochondrial Properties of Gossypol Enantiomers, Molecular Pharmacology 37:840-847 (11990).
Benz et al., Gossypol Effects on Endothelial Cells and Tumor Flow, Life Sciences 49:67-72 (1991).
Blackstaffe et al., Cytotoxicity of gossypol enantiomers and its quinone metabolite gossypolone in melanoma cell lines, Melanoma Research 7:364-372 (1997).
Bourinbaiar et al., Comparative in vitro study of contraceptive agents with anti-HIV activity: *Gramicidin, nonoxynol-9, and gossypol*, Contraception 49:131-137 (1994).
Brandes et al., New Drugs in Recurrent High Grade Gliomas, Anticancer Research 20:1913-1920 (2000).
Brandes et al., New therapeutic agents in the treatment of recurrent high-grade gliomas, Forum Trends in Experimental and Clinical Medicine 10:121-131 (2000).
R. Bruno et al., J. Clin. Oncol., 16:187-196 (1998).
Bushunow et al., Gossypol Treatment of Recurrent Adult Malignant-Gliomas, Proceedings of ASCO, 14:282 (1995).
Bushunow et al., Gossypol Treatment of recurrent adult malignant gliomas, Journal of Neuro-Oncology 43:79-86 (1999).

Chang et al., Antiproliferative and Antimetastatic Effects of Gossypol (GP) on Mat-Lylu-Bearing Rats, FASEB Journal, 6:3794 (1992).

Chang et al., Prostate, begin hypertrophy and prostatic carcinoma: A study of cell biology of prostate and chemotherapy for prostatic hypertrophy and prostatic cancer, Dissertation Abstract International, 55:4330-B (1995).

Chang et al., Potential of Gossypol (GP) and Transforming Growth Factor-$\beta$, (TGF-$\beta_1$) as Inhibitors of Canine Prostate Growth, FASEB Journal, 9:4813-4814 (1995).

Chang et al., Antiproliferative and Antimetastatic Effects of Gossypol on Dunning Prostate Cell-Bearing Copenhagen Rats, Research Communications in Chemical Pathology and Pharmacology 79:293-312 (1993).

Chen et al., Application of 2D NMR Techniques in the Structure Determination of Ganosporelactone A and B, ACTA Pharmaceutica Simica 26:430-436 (1991).

Coyle et al., In-Vitrop and in vivo cytotoxicity of gossypol against central nervous system tumor cell lines, Journal of Neur-Oncology 19:25-35 (194).

Dallacker er al. Uber Gossypol- und Hemigossypol-Derivate—Darstellung von Hydroxy-methyl-naphto[1,3]dioxolen, Chemiker-Zeitung 113:5-11 (1989).

Dallacker et al., Darstellung von Methyl-isopropyl-naphtholderivaten durch Pd-katalysierte Cyclocarbonylierung, Chemiker-Zeitung 114:144-147 (1990).

Dao et al., Synthesis and cytotoxicity of gossypol related compounds, Eur. J. Med. Chem. 35:805-813 (2000).

Darzynkiewicz et al., Cytometry in Cell Necrobiology: Analysis of Apoptosis and Accidental Cell Death (Necrosis), Cytometry 27:1-20 (1997).

Data et al., A Study of the Derivatives of (+)-Gossypol, Indian Journal of Chemistry 10:691-693 (1972).

Davila et al., Toxicological Studies of Gossypol in Primary Culture of Postnatal Rat Hepatocytes, Journal of Molecular and Cellular Toxicology, 4:161-170 (1991).

Deck et al., Gossypol and Derivatives: A New Class of Aldose Reductase Inhibitors, J. Med. Chem. 34:3301-3305 (1991).

DeMartino et al., Electron microscopic and biochemical studies of the effect of Gossypol on Ehrlich ascites tumor cells, Caryologia, International Journal of Cytology, Cytosystematics and Cytogenetics 35:114-115 (1982).

de Peyster et al., Genetic toxicity studies of gossypol, Mutation Research 197:293-312 (1993).

De-yu et al., Mutagenicity of gossypol analyzed by inductio of meiotic micronuclei in vitro, Mutation Research 208:69-72 (1988).

Dhaliwal et al., Cytogenetic Analysis of a Gossypol-Induced Murine Myxosarcoma, Journal of the National Cancer Institute, 78:1203-1209 (1987).

A. Degterev et al., Nat. Cell Biolog., 3:173-182 (2001).

Dogliotti et al., Cytotoxic chemotherapy for adrenocortical carcinoma, Minerva Endocrinologica, 20:105-109 91995).

Edwards et al., Sysnthesis of Gossypol and Gossypol Derivatives, Journal of the American Oil Chemists' Society 47:441-442 (1970).

Finaly et al., Mechanism of the Gossypol Inactivation of Pepsinogen, Journal of Biological Chemistry 248:4827-4833 (1973).

Fish et al., The Photo-epimerisation of Gossypol Schiff's Bases, Tetrahedron: Asymmetry 6:873-876 (1995).

Flack et al., Treatment of adrenocortical carcinoma with gossypol, Proceedings of American Association for Cancer Research 31:198 (1990).

Flack et al., Oral Gossypol in the Treatment of Metastatic Adrenal Cancer, Journal of Clinical Endocrinology and Metabolisms, 76:1019-1024 (1993).

Floridi et al., The Effect of the Association of Gossypol and Lonidamine on the Energy Metabolism of Ehrlich Ascites Tumor Cells, Experimental and Molecular Pathology 38:322-335 (1983).

Floridi et al., The Effect of Gossypol on Lonidamine on Electron Transport in Ehrlich Ascites Tumor Mitochondria, Experimental and Molecular Pathology 40:246-261 (1984).

Ford et al., Modulatio nof resistance of alkylating agents in cancer cell by gossypol enantiomers, Cancer Letters 56:85-94 91991).

Gilbert et al., Antiproliferative Activity of Gossypola nd Gossypolone on Human Breast Cancer Cells, Life Sciences 57:61-67 (1995).

Gonzalez-Garza et al. Cytotoxic Effects of Gossypol and Vitamin E on Human and Rat Lymphocytes and Spermatozoa, Nutrition Reports International (1995).

Gorczyca et al., The Cell Cycle Related Differences in Susceptibility of HL-60 Cells to Apoptosis Induced by Various Antitumor Agents, Cancer Research 53:3186-3192 (1993).

Grankvist, Gossypol-Induced Free Radical Toxicity to Isolated Islet Cells, Int. J. Biochem. 21:853-856 (1989).

Hamasaki et al., Gossypol, a potent inhibitor of arachidonate 5- and 12-lipoxygenases, Biochimica et Biophysica Acta 834:37-41 (1985).

Han et al., Gossypol in the Treatment of Endometriosis and Uterine Myoma, Chontr. Gynec. Obstet. 16:268-270 (1987).

Haroz et al., Tumor Initiating And Promoting Activity of Gossypol, Toxicology letters, 72 (1980).

Haspel et al., Cytocidal Effect of Gossypol on Cultured Murine Erythroleukemia Cells is Prevented by Serum Protein, Journal of Pharmacology and Experimental Therapeutics 229:218-225 (1984).

J. Hirth et al., Clin. Cancer Res., 6:1255-1258 (2000).

Heinstein et al., The Biosynthesis of Gossypol, Biochemistry 28:1342-B (1967).

Hendricks et al., Hepatocarcinogenicity of Glandless Cottonseeds and Cottonseed Oil to Rainbow Trout (Salmo gairdnerii), Science 208:309-311 (1980).

Herve et al., Contraceptive gossypol blocks cell-to-cell communication in human and rat cells, European Journal of Pharmacology 313:243-255 (1966).

Hong et al., Study of the Effects of Acetate Gossypol High Energy Shock Waves (HESW) and Their Combination on the Human Bladder Cancer Cell Line $BT_{5637}$, ACTA Anatomica Sinica 25:291-296- (1994).

Hu et al., Gossypol Effects on Cultured Normal and Malignant Melanocytes, In Vitro Cellular & Development Biology 22:583-588 (1986).

Hu et al., Gossypol Inhibits Basal And Estrogen ($E_2$)-Stimulated DNA Synthesis in Human Breast Carcinoma (HBC) Cells, FASEB Journal, 7:3982 (1993).

Hu et al., Gossypol Inhibits Basal And Estrogen-Stimulated DNA Synthesis in Human Breast Carcinoma Cells, Life Sciences 53:433-439 (1993).

Hu et al., Presence of antitumor activities in the milk collected from gossypol-treated dairy cows, Cancer Letters 87:17-23 (1994).

Huang et al., Resolution of Racemic Gossypol, Journal of Ethnopharmacology 20:13-20 (1987).

Huchinson et al., The mechanism of gossypol acetic acid cytotoxicity, Dissertation Abstracts Inernational, 59:1612-B (1998).

Hutchinson et al., Attenuation of Gossypol Cytotoxicity by Cyclic AMP in a Rat Liver Cell Line, Toxicology and Applied Pharmacology 151:311-318 (1998).

Jaroszewski et al., Action of Gossypol and Rhodamine 123 on Wild type and Multidrug-resistant MCF-7 Human Breast Cancer Cells: [31]P Nuclear Magnetic Resonance and Toxicity Studies, Cancer Research 50:6936-6943 (1990).

Jarvis et al., INduction of Apoptotic DNA Fragmentation and Cell Death in HL-60 Human Promyelocytic Leukemia Cells by Pharmacological Inhibitors of Protein Kinase C[1], Cancer Research 54:1707-1714 (1994).

Jiang et al., Inhibitory Action of Gossypol on the Growth of MAT-LyLu Prostate Cancer Cells is Associated with Stimulation of Transforming Growth Factor-$\beta_1$ (TGF-$\beta_1$), Biology of Reproduction 60:252.

Jiang et al., Differing Effects of Gossypol on MAT-LYLU Cells and MAT-LYLU Cells Isolated From Metastasized Lung of MAT=LYLU Cell-Bearing Copenhagen Rats, Society for the Study of Reproduction 58:89.

Jiang et al., The Effffects of Gossypol on the Invasiveness of MAT-Lylu Cells and MAT-Lylu Cells from the Metastasized Lungs of MAT-LyLu-Bearing Copenhagen Rats, Anticancer Research 20:4591-4598 (2000).

Jia-xin et al., Studies on the Synthesis of Gossypol Derivatives and Their Antifertility Action, Reproduction and Contraception 6:48:51 (1986).

Joingfang et al., Of Gossypol in Mice, Rats and Human Tumor Cell Lines and Its Possible Mechanism, ACTA Academiae Medicinae Sinicase 8:486-488 (1986).

Jolad et al., Tumor-Inhibitory Agent from *Montezuma speciosissima* (Malvaceae), Journal of Pharmaceutical Scicnes 64:1889-1890 (1975).

Joseph et al., Cytotoxicity of enantiomers of gossypol, Br. J. Cancer 54:511-513 (1986).

Jung et al., Recent Studies on Natural Products as Anti-HIV Agents, Current Medicinal Chemistry 7:649-651 (2000).

Kai et al., Resolution of Racemic Gossypol, J. Chem. Soc., Chem. Commun. 3:168:169 (1985).

Kaplan et al., Metabolism of breast cancer cells as revealed by non-invasive magnetic resonance spectroscopy studies, Breast Cancer Research and Treatment 31:285-299 (1994).

Keller et al., Novel pharmacophore-based methods reveal gossypol as a reverse transcriptase inhibitors, Journal of Molecular Graphics and Modelling 5346:1-9 92002).

Keniry et al., Magnetic Resonance Spectroscopy (MRS) and Imaging (MRI) in the Evaluation of Tumor Growth and Chemotherapy Response, Proceedings of AACR 27:384 (1986).

Keniry et al., The Effect of Gossypola nd 6-Aminonicotinamide on Tumor Cell Metabolism: A $^{31}$P-Magnetic Resonance Spectroscopic Study, Biochemical and Biophysical Research Communications 164:947-953 (1989).

Kim et al., Comparative In Vitro Spermicidal Effects of (±)-Gossypol, (+)-Gossypol, (−)-Gossypol and Gossypolone, Contraception 30:253-259 (1984).

Koll et al., A Phase 1 Study of Gossypol (GP) in HIV-Infected Patients (pts) in Mexico, Abstracts of the 33rd ICAC 245-687.

Koryakin et al., Ultrasound investigation of blood supply in scrotal organs, 10th World Congress on Human Reproduction 307 (1999).

Latronico et al., Extensive Personal Experience Adrenocortical Tumors, Journal of Clinical Endocrinology and Metabolism 82:1317-1324 (1997).

LaVoie et al., Investigation of Intracellular Signals Mediating the Anti-Apoptotic Action of Prolactin in Nb2 Lymphoma Cells, Society for Experimental Biology and Medicine 257-269 (1995).

Lee, Novel Antitumor Agents from Higher Plants, Medical Research Reviews, 19:569-596 (1999).

Lee et al., Plant PHenolic Compounds as Cytotoxic Antitumor Agents, American Chemical. Society 29:367-379 (1992).

Lefeng et al., Clinical Effects and Experimental Study on Gossypol in Endometriosis, Chin, J. Integr Med. 9(8):451-464 (1989).

Levine, Inhibition of the A-23187-Stimulated Leukotriene And Prostaglandin Biosynthesis of Rat Basophil Leukemia (RBL-1) Cells By Non-Steroidal Anti-Inflammatory Drugs, Anti-Oxidants, and Calcium Channel Blockers, Biochemical Pharmacology 32:3023-3025 (1983).

Li et al., DNA-Breaking Versus DNA-Protecting Activity of Four Phenolic Compounds in vitro, Free Rad. Res. 33:551-566 (2000).

Llian et al., Hepatoma Initiating and Promoting Effects of Gossypol, ACTA Academiae Medicinae Sinicase (1985).

Liang et al., Developing gossypol derivatives with enhanced antitumor activity, Investigational New Drugs 13:181-186 (1995).

Liqueros et al., The antiproliferative Effects of Gossypol and the Retinoblastoma Gene Protein, Clinical Pharmacology & therapeutics 57:206 (1995).

Liqueros et al., Gossypol inhibition of mitosis, cyclin D1 and Rb protein in human mammary cancer cells and cyclin-D1 transfected human fibrosarcoma cells, British Journal of Cancer 76:(1):21-28 (1997).

Lin et al., Selective Inhibition of Human Immunodeficiency Virus Type 1 Replication by the (−) but Not the (+) Enantiomer of Gossypol, Antimicrobial Agents and Chemotherapy, 2149-2151 (1989).

Lin et al., Anti-HIV-1 Activity and Cellular Pharmacology of Various Analogs of Gossypol, Biochemical Pharmacology 46:251-255 (1993).

Lin et al., Gossypol and tamoxifen prevent estrogen-induced renal carcinogenesis in hamsters, Proceedings of the American Association for Cancer Research 36:391-2329 (1995).

Majumdar et al., Genotoxic Effects of Gossypol Acetic Acid on Cultured Murine Erythroleukemia Cells, Environmental and Molecular Mutagenesis 18:212-219 (1991).

Matlin et al., Large-Scale Resolution of Gossypol Enantiomers for Biological Evaluation, Contraception 37:229-237 (1988).

McSheehy et al., Gossypol, a cytoxic agent, may uncouple respiration of Ehrlich ascites tumour cells, Biochemical Society Transactions 16:616-617 (1988).

Meiling, Gossypol Treatment for Menopausal Functional Bleeding, Myoma of Uterus and Endometriosis—Preliminary Report, ACTA Academiae Medicine Sinicae 2:167-169 (1980).

Meltzer et al., A Regioselective Route to Gossypol Analogues: The Synthesis of Gossypol and 5,5'-Didesisopropyl-5,5'-diethylgossypol, J. Org. Chem. 50:3121-3124 (1985).

Fujii et al., "Effect of cerulenin, an inhibitor of fatty acid synthesis, on the immune cytolysis of tumor cells" Jpn. J. Exp. Med Jun. 1986;56(3):99-106 (Abstract only).

Gossypol, Xian Oil 7 Fat Works, Drugs of the Future, vol. 21, No. 5, 1996.

Meyers et al., The synthesis of (S)-(+)-gossypol via an asymmetric Ullmann coupling, Chem. Commun., 1573-1584 (1997).

Moh et al.., Effect of Gossypol (GP) on a 5α-Reductase and a 3α-Hydroxysteroid Dehydrogenase (3α-HSD) in Adult Rat Testes, FASEB Journal 6342 (1992.

Mohan, Problems and Perspectives in the Design of Anti-HIV-1 Agents, Drug Development Research 29:1-17 (1993).

S.W. Muchmore et al., Nature, 381:335-341 (1996)).

Mushtaq et al., Gossypol (GP) Inhibits in Vitro Porcine Oocyte Maturation and Early Embryonic Development in Modified Simple Media, Society for the Study of Reproduction, 52:172 (1998).

Naik et al., Preclinical studies of gossypol in prostate carcinoma, International Journal of Oncology 6:209-213 (1995).

Nayak et al., Induction of Sister Chromatid Exchanges and Chromosome Damage by Gossypol in Bone Marrow Cells of Mice, Teratogenesis, Carcinogenesis, and Mutagenesis 6:83-91 (1986).

Newman et al., Pharmacokinetics and toxicity of 120-hour continuous-infusion hydroxyurea in patients with advanced solid tumors, Cancer Chermother Pharmacol 39:254-258 (1997).

Ng et al., Anti-Human Immunodeficiency virus (Anti-HIV) Natural Products with Special Emphasis on HIV Reverse Transcriptase Inhibitors, Life Sciences 61:933-949 (1997).

Ognyanov et al., Synthesis of Gossypol Analogues, Helvetica Chimica ACTA 72:353-360 (1989).

Ohuchi et al., Inhibition of gossypol of tumor promoter-induced arachidonic acid metabolism in rat peritoneal macrophages, Biochimica et Biophysica Acta, 971:85-91 (1988).

Olgiati et al., Gossypol Inhibition of Adenylate Cyclase, Archives of Biochemistry and Biophysics 231:411-415 (1984).

Papageorgiou et al., A New Method for the Isolation of Gossypol From Cottonseed-Oil Fatty Acids, Chimika Chronika 7:101-109(1978).

Perez et al., Studies on spermatogenesis and apoptosis in the bovine, Disseration Abstracts International 50:526-B (1999).

Phung et al., Isolation and Purification of Gossypol in Cotton Seeds of Vietnam, Tap chi Hoa hov, 35:91-93 (1997).

Pirogov et al., Postoperative Bronchopleural Complications in Combined Treatment of Pulmonary Cancer, Issues of Oncology, 20:24-28 (1974).

Polsky et al., Inactivation of Human Immunodeficiency Virus (RIV) By Gossypol (GP), Clinical Research 35(3)487A (1987).

Polsky et al., Inactivation of Human Immunodeficiency Virus in Vitro by Gossypol, Contraception, 39:579-587 (1989).

Przybylski et al., Spectroscopic studies and PM5 semiempirical calculations of new schiff bases of gossypol with amino derivatives of crown ethers, Journal of Molecular Structure, 16:04-1-9 (2002).

Qian, Gossypol: A Potential Antifertility Agent for Males, Ann. Rev. Pharmacol. Toxicol. 24:329-60 (1984).

Qui et al., The Search for Gene(s) Conferring Sensitivity to Cell Killing by Gossypol, The FASEB Journal 13:A151A (1999).

J. O'Quigley et al., Biometrics 46:33-48 (1990).

Quintana et al., Gossypol-induced DNA breaks in rat lymphocytes are secondary to cytotoxicity, Toxicology Letters 117:85-94 (2000).

Rao et al., Antitumor effects of gossypol on murine tumors, Cancer Chemother Pharmacol. 15:20-25 (1985).

Razakantoanina et al., Antimalarial activity of new gossypol derivatives, Parasitol Res. 86:665-668 (2000).

Reidenberg, Studies of gossypol in the treatment of cancer, Reproductive Medicine, 305-308.

Reidenberg et al., Gossypol Treatment of Metastatic Adrenal Cancer, Clinical Pharmacology and Therapeutics, 51:P1-96 (1992).

Rekha et al., Inhibition of Human Class 3 Aldehyde Dehydrogenase, and Sensitization of Tumor Cells that Express Significant Amounts of this Enzyme to Oxazaphosphorines, by the Naturally Occurring Compounds Gossypol, Enzymology and Molecular Biology of Carbonyl Metabolism 6, 133-146 (1996).

Resnick et al., Comparative Evaluation of Sperimicidal Agents with Virucidal Activity Against HIV, IXth International Conference on AIDS, 11:PO-C22-3154 (1993).

Rosenberg et al., Biochemical Basis for the Gossypol-induced Inhibition of DNA Replication in Mammalian Cells, American Association for Cancer Research, 29:1291 (1988).

Royer et al., Inhibition of Human Immunodeficiency Virus Type I Replication by Derivatives of Gossypol, Pharmacological Research, 24:407-412 (1991).

G. Rassidakis et al., Amer. J. Path., 159:527-535 (2001).

J.C. Reed et al., Ann. Oncol., 5:61-65 (1994).

Sampath et al., A Rapid Procedure for the Resolution of Racemic Gossypol, J. Chem. Soc., Chem. Commun., 649-650 (1986).

Schinazi et al., Insights Into HIV Chemotherapy, Aids Research and Human Retroviruses, 8:963-990 (1992).

A.F. Schott et al., Oncogene, 11:1389-1394 (1995).

Seidman et al., Gossypol in Advanced Breast Cancer, Journal of Investigative Medicine 46:213A (1998).

Seidman, Chemotherapy for Advanced Breast Cancer: A Current Perspective, Seminars in Oncology, 23:55-59 (1996).

Shelly et al., Stereo-specific cytotoxic effects of gossypol enantiomers and gossypolone in tumour cells lines, Cancer Letters, 135:171-180 (1999).

Shelly et al., Structure-activity studies on gossypol in tumor cell lines, Anti-Cancer Drugs, 11:209-216 (2000).

S. Shi et al., J. Histochem. Cytochem., 39:741-748 (1991).

Shidaifat et al., Differential regulation of gene expression by gossypo0l: A potential inhibitor of prostate cell growth, Dissertation Abstracts International, 57:6097-B (1997).

Shidaifat et al., Inhibition of human prostate cancer cells growth by gossypol is associated with stimulation of transforming growth factor-β, Cancer Lettesr 107:37-44 (1996).

Shidaifat et al., Gossypol Arrests Human Benign Prostatic Hyperplastic Cell Growth at G0/G1 Phase of the Cell Cycle, Anticancer Research 17:1003-1010 (1997).

Sinnhuber et al., Dietary Factors and Hepatoma in Rainbow Trout (*Salmo gairdneri*). *Π*. Cocarcinogenesis by Cyclopropenoid Fatty Acids and the Effect of Gossypol and Altered Lipids on Aflatoxin-Induced Liver Cancer, Journal of the National Cancer Institute, 41:1293-1299 (1968).

Stein et al., A preliminary clinical study of gossypol in advanced human cancer, Cancer Chemother Pharmacol 30:480-481 (1992).

Sugimoto et al., Differential proliferative rseponses to the (−)-enantiomer of gossypol in cultured human breat epithelial and stromal cells, American Association for Cancer Research 40:4 (1999).

Tai, Rat Basophilic Leukemia-1 Cell Possesses 12-Lipoxygenase and 5-Lipoxygenase activities which are specifically inhiibited by gossypol acetic acid, Japanese Journal of Allergology 33:1040-1046 (1984).

Tan et al., Evaluation of Natural Products As Inhibitors of Human Immunodeficiency Virus Type 1 (HIV-1) Reverse Transcriptase[1], Jouranl of Natural Products, 54:143-154 (1991).

Tanphaichitr et al., Direct Effect of Gossypol on TR-ST Cells: Perturbation of Rhodamine 123 Accumulation in Mitochondria, Biology of Reproduction, 31:1049-1060 (1984).

Tao et al., The Effects of Gossypol on Human BPH Cells In Vitro, 21:31 (1994).

Teng et al., c-MYC Protein Expression in spermatocytes During Gossypol-Induced Apoptosis, Molecular Biology of the Cell, 364a:2116 (1997).

Teng et al., Biphasic c-Myc Protein Expression During Gossypol-Induced Apoptosis in Rat Spermatocytes, Contraception 57:117-123 (1998).

Teng, C-Fos Protein Expression in Apoptotic Rat Spermatocytes Induced by Gossypol, Contraception 57:281-286 (1998).

Thoenes et al., Cytotoxic Effects of Adriamycin, Bleomycin, Gossupol and Hydroxyanisol to Cultured Human Malignant Melonoma Cells, Journal of Cancer Research and Clinical Onocology, 113:D-THER:12, S46 (1987).

Thomas et al., Effects of Gossylpol on the Cell Cycle Phases in T-47D Human Breat Cancer Cells, Anticancer Research 11:1469-1476 (1991).

D.K. Trask et al., Laryngoscope, 112:638-644 (2002).

Troll et al., Free Oxygen Radicals: Necessary Contributors to Tumor Promotion and Cocarcinogenesis, Proceedings of the 14th International Symposium of The Princess Takamatsu Cancer Research Fund, 207-218 (1984).

Tso, Gossypol Inhibits Ehrlich Ascites Tumor Cell Proliferation, Cancer Letters 24:257-261 (1984).

Tuszynski et al., Differential Cytotoxic Effect of Gossypol on Human Melanoma, Colon Carcinoma, and Other Tissue Culture Cell Lines, Cancer Research 44:768-771 (1984).

Vander Jagt et al., Gossypol: Prototype of Inhibitors Targeted to Dinucleotide Folds, Current Medicinal Chemistry 7:479-498 (2000).

Van Poznak et al., Oral Gossypol in the treatment of patients with refractory metastatic breast cancer: A phase I/II clinical trial, Breat Cancer Research and Treatment 66:239-248 (2001).

Vlietinck et al., Plant-Derived Leading Compounds for Chemotherapy of Human Immunodeficiency Virus (HIV) Injection, PlantaMedica 64:97-109 (1998).

Wang et al., Effect of Gossypol on DNA Synthesis and Cell Cycle Progression of Mammalian Cells in Vitro, Cancer Research 44:35-38 (1984).

Wang et al., Cytotoxic effect of gossypol on olonn carcinoma cells, Life Sciences 67:2663-2671 (2000).

P. Watkins, Pharmacogenetics, 4:171-184 (1994).

Wichmann et al., Inhibiting herpes simplex virus tyupe 2 infection in human epithelial cells by gossypol, a potent spermicidal and contraceptive agent, Am. J. Obstet. Gynecol. 142:593-594 (1982).

Wu et al., Pharmacokinetics of (±)-, and (+)-, and (−)-gossypol in humans and dogs, Clinical Pharmacology & Therapeutics 39:613-618 (1996).

Wu et al., An in Vitro and in Vivo Study of Antitumor Effects of Gossypol on Human SW-13 Andrenocortical Carcinoma, Cancer Research 49:3743-3758 (1989).

Wu et al., In vitro antitumor activity of gossypol alone or in combination with amsacrine, European Journal of Pharmacology 183:230 (1990).

Xueqing et al., Clinical Observation and Experimental Study of Gossypol in Treatment of Dysfunctional Menorrhagia, Endometriosis and Fibromyoma of Uterus, Chinese Journal of Integrated Traditional and Western Medicine8:197 (1988).

Ye et al., The Modulation of Gap Junctional Communication by Gossypol in Various Mammalian Cell Lines in Vitro, Fundamental And Applied Toxicology 14:817-832 (1990).

Ye et al., Toxicity of a Male Contraceptive, Gossypol, in Mammalian Cell Cultures, In Vitro 19:53-57 (1983).

Yikang et al., Studies on Resolution of Racemic Gossypol, Scientia Sinica 30:297-303 (1987).

Ying et al., Studies on Frequencies of Sister Chromatid Exchange in Peripheral Blood Lymphocytes Before and After Gossypol Treatment, Proc. DAMS and PUMC 1:34-36 (1986).

Youfang et al., Ultrastructural Changes of Smooth Muscle Cells in Leiomyoma and Myometrium of Human Uterus after Gossypol Treatment, ACTA Academiae Medicinae Sinicae, 9:299-301 (1987).

Yu, Probing Into the Mechanism of Action, Metabolism and Toxicity of Gossypol by Studying its (+)- And (−)- Stereoisomers, Journal of Ethnopharmacology 20:65-78 (1987).

Zhang et al., The (−)-enantiomer of gossypol inhibits proliferation of stromal cells derived from human breast adipose tissues by enhancing transforming growth factor β₁ production, International Journal of Oncology 13:1291-1297 (1998).
Wu et al., J. Chromatography 433:141 (1988).
Shen et al., Ch. J. Magnetic Resonance 20:373 (2003).
Meyers et al., Tetrahedron 54:10493 (1998).
Brzezinski et al., J. Mol. Structure 230:261 (1990).
Matlin et al., J. Liquid Chromatography 12:1485 (1989).
Jaroazewski et al., Chirality 4:216 (1992).
Przybylski et al., J. Mol. Structure 691:227 (2004).
Przybylski et al., J. Mol. Structure 654:167 (2003).
Przybylski et al., J. Mol Structure 569:147 (2001).
Haas et al., J. Org. Chem. 30:4111 (1965).
Przyblski et al., J. Mol. Structure 699:65 (2004).
Dao, Disssertation, University of Paris XI (2002).

Boyfield et al., "n-(substituted-phenyl)piperazines:" Bioorganic And Medicinal Chemistry Letters, 6:1227-32 (1996).
Rao, "Agents acting on the central nervous system. XIII:", Journal of Medicinal Chemistry 13:516-22 (1970).
Singh et al., "Antihypertensive and cns depressant properties of 3-(gamma-p-fluorobenzoylpropyl)2,3,4,4a,5,6-hexahydro-a)h)-pyrazinol(1-2-a)quinoline hydrochloride", Experientia 29:1529-30 (1973).
Singh et al., "Pharmacological studies on 3[gamma-(p-fluorobenzoly)propyl]-2,3,4,4a,5,6,hexahydro -1-(H)pyrazinol(1,2,-a)quinoline hydrochloride (Compound 69/83)" Arrzneimittel Forschung Drug Research 28:1641-4 (1978).

* cited by examiner

CRYSTAL STRUCTURE OF THE ACTIVATED INSULIN RECEPTOR TYROSINE KINASE DOMAIN

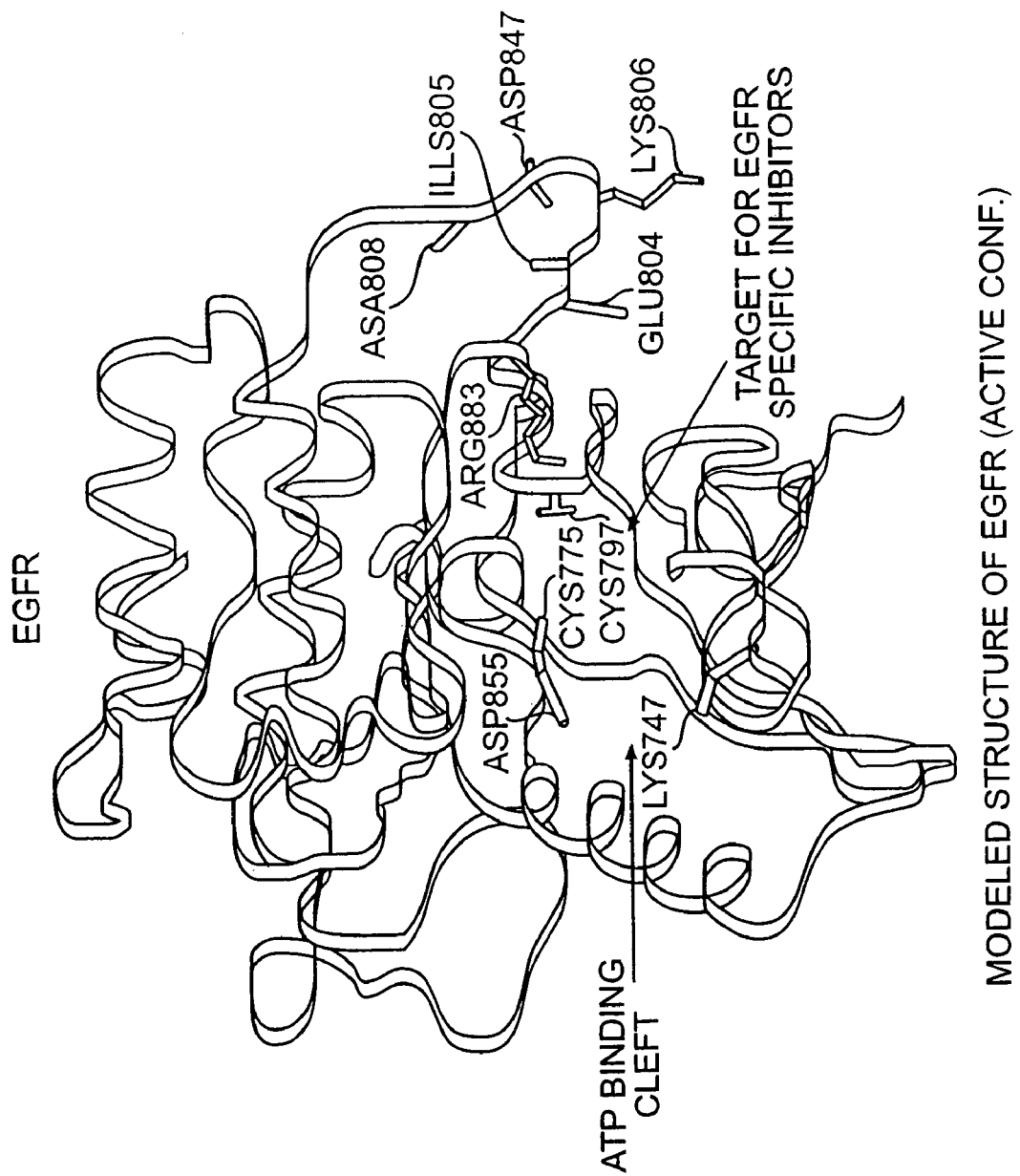

B17

Chemical Structure of
B17

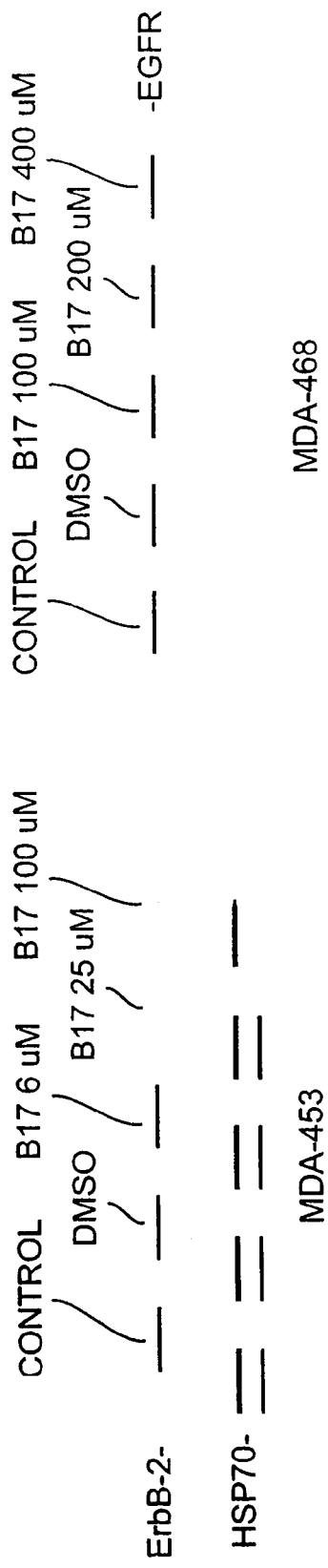
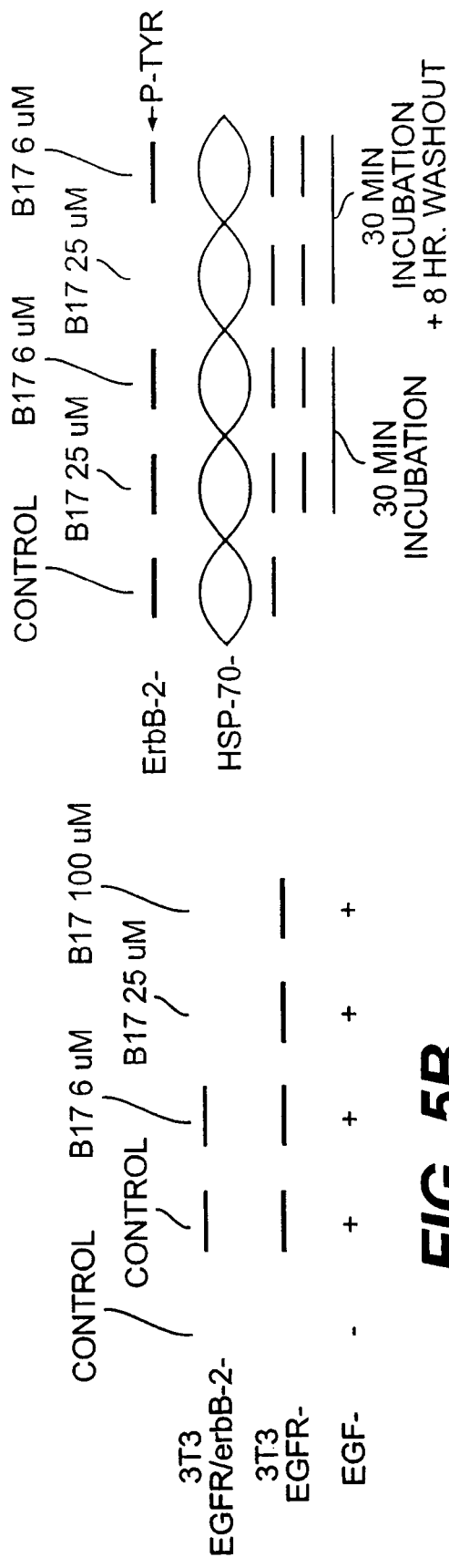
FIG. 5A
FIG. 5B
FIG. 5C

ERBB-2 SELECTIVE SMALL MOLECULE KINASE INHIBITORS

CROSS REFERENCE TO RELATED APPLICATION

This application claims priority from U.S. Provisional Patent Application Serial No. 60/221,515, filed Jul. 28, 2000, the entirety of which is incorporated herein by reference.

FIELD OF THE INVENTION

The present invention relates to a novel method of prevention or treatment of diseases where signal transduction pathways mediated by erbB-2 tyrosine kinase play a significant role. Examples thereof include abnormal cell proliferation, including cancer, particularly, breast cancer.

BACKGROUND OF THE INVENTION

For mammalian cells to survive, they must be able to respond rapidly to changes in their environment. Furthermore, for cells to reproduce and carry out other cooperative functions, they must be able to communicate efficiently with each other.

Cells most frequently adapt to their environment and communicate with one another by means of chemical signals. An important feature of these signaling mechanisms is that in almost all cases a cell is able to detect a chemical signal without it being necessary for the chemical messenger itself to enter the cell. This permits the cell to maintain the homeostasis of its internal environment, thereby permitting the cell to respond to its external environment without being adversely affected by it.

These sensing functions are carried out by a variety of receptors, which are dispersed on the outer surface of the cell and function as "molecular antennae." These receptors detect an incoming messenger and activate a signal pathway that ultimately regulates a cellular process such as secretion, contraction, metabolism or growth.

In the cell's cellular plasma membrane, transduction mechanisms translate external signals into internal signals, which are then carried throughout the interior of the cell by chemicals known as "second messengers."

In molecular terms, the process depends on a series of proteins within the cellular plasma membrane, each of which transmits information by inducing a conformational change in the protein next in line. At some point, the information is assigned to small molecules or even to ions within the cell's cytoplasm, which serve as the above-mentioned second messengers. The diffusion of the second messengers enables a signal to propagate rapidly throughout the cell.

Abnormal cell signaling has been associated with cancer diseases. Cell signaling plays a crucial role in cell growth, proliferation and differentiation. Thus, when normal cell signaling pathways are altered, uncontrolled cell growth, proliferation and/or differentiation can take place, leading to the formation and propagation of cancer.

Cancer is the leading cause of death, second only to heart disease in both men and women. Breast cancer is the most common tumor in women, representing 32% of all new cancer cases and causing 18% of cancer-related deaths of women in the United States. In the fight against cancer, numerous techniques have been developed and are the subject of current research to understand the nature and cause of the disease, and to provide techniques for the control or cure thereof One promising avenue for the development of cancer treatments is based on blocking abnormal cell signaling pathways. Particular efforts are directed to the elucidation and regulation of the activity of receptor and trans-membrane proteins.

The human epidermal growth factor (EGF) is a six kilodalton (kDa), 53 amino acid, single-chain polypeptide which exerts its biological effect by binding to a specific 170 kDa cell membrane receptor (EGF-Rc). The human EGF-Rc consists of an extracellular domain with a high cysteine content and N-linked glycosylation, a single transmembrane domain, and a cytoplasmic domain with tyrosine kinase activity.

Many types of cancer display enhanced EGF-Rc expression on their cell surface membranes. Enhanced expression of the EGF-Rc can increase signalling via receptor-mediator pathways which lead to pleiotropic biological effects including excessive proliferation and metastasis. Examples include prostate cancer, breast cancer, lung cancer, head and neck cancer, bladder cancer, melanoma, and brain tumors.

In breast cancer, expression of the EGF-Rc is a significant and independent indicator for recurrence and poor relapse-free survival. The epidermal growth factor receptor (EGF-Rc) of cancer cells therefore represents a potential target for biotherapy.

EGFR and its physiologic ligands, epidermal growth factor (EGF) and transforming growth factor alpha (TGF alpha), play a prominent role in the growth regulation of many normal and malignant cell types. One role the EGF receptor system may play in the oncogenic growth of cells is through autocrine-stimulated growth. Cells which express EGFR and secrete EGF and/or TGFalpha can stimulate their own growth, thereby creating a cancerous condition.

An autocrine growth stimulatory pathway analogous with that proposed for epidermal growth factor receptor and its ligands may also be employed by a growing list of oncogene encoded transmembrane proteins that have a structure reminiscent of that of the growth factor receptors.

The HER-2/neu or c-erbB-2 oncogene belongs to the erbB-like oncogene group, and is related to, but distinct from EGFR. The ErbB-2 gene encodes a 185 kD transmembrane glycoprotein that has partial homology with other members of the EGFR family. The expressed protein has been suggested to be a growth factor receptor due to its structural homology with EGFR. However, known EGFR ligands, such as EGF or TGF. alpha do not bind to $p^{185}$-erbB-2.

The erbB-2 oncogene has been demonstrated to be implicated in a number of human adenocarcinomas leading to elevated levels of expression of the $p^{185}$ protein product. For example, the erbB-2 oncogene has been found to be amplified in breast, ovarian, gastric and even lung adenocarcinomas. Furthermore, the amplification of the c-erbB-2 oncogene has been found in many cases to be a significant, if not the most significant, predictor of both overall survival time and time to relapse in patients suffering from such forms of cancer. Carcinoma of the breast and ovary account for approximately one-third of all cancers occurring in women and together are responsible for approximately one-fourth of cancer-related deaths in females.

Significantly, the c-erbB-2 oncogene has been found to be amplified in 25 to 30% of human primary breast cancers and it has been associated with a high risk of relapse and death. In breast cancers with erbB-2 overexpression abnormal cell proliferation is believed to be caused by extremely high tyrosine kinase activity and the resulting high level of signal transduction.

Overexpression of HER-2 has also been found to be associated with increased resistance to chemotherapy or patients with elevated levels of HER-2 respond poorly to many drugs. It is believed that decreasing the levels of HER-2 will allow chemotherapeutic drugs to be more effective. Therefore, therapies targeted at erbB-2 have the great therapeutic potential for the treatment of breast cancers.

In view of the above, the development of new and potent anti-breast cancer drugs and the design of treatment protocols directed at the regulation of erbB-2 activity is an exceptional focal point for research in the modern therapy of breast cancer. Drug targeting is a particularly attractive approach for killing malignant cells, when leaving normal tissue unharmed is achieved.

ErbB-2 is a clinically proven therapeutic target for breast cancer. Indeed, the recently completed phase M clinical trial of anti-Her2 Herceptin provide evidence that systemic administration of Herceptin, alone and in combination with cytotoxic chemotherapy in patients with erbB-2 overexpressing prinary tumors, can increase the time to recurrence and overall response rates in metastatic breast cancer. Herceptin is recognized as the first in what promises to-be a wave of therapies attacking cancer at its genetic roots.

Certain limitations are associated with large molecule strategies, including poor delivery, poor in vivo stability, possible immune response and high cost. Accordingly, it is highly desirable to provide therapies based on small molecules targeted at interfering with erbB receptor-mediated signal transduction pathways (including erbB-2, erbB-3 and erbB4). Compared to therapies based on large drug molecules, such as therapeutic antibodies, small molecule drug therapies have a number of advantages, including good oral availability and low cost.

A number of criteria should be considered in the development of small molecule erbB-2 kinase inhibitors, including good potency, selectivity, cell permeability, bioavailability, appropriate pharmacokinetics and non-toxicity.

In breast cancers with erbB-2 overexpression, abnormal cell proliferation is caused by the extremely high tyrosine kinase activity and resulting high level of signal transduction. Drugs blocking this extremely high erbB-2 tyrosine kinase activity could have the potential to shut down signaling pathways mediated by erbB-2. Thus, erbB-2 kinase inhibitors that are capable of entering the cell, blocking tyrosine kinase activity and shutting down the signal transduction pathway mediated by erbB-2 may be used as potential therapeutic agents for the treatment of breast cancer. Furthermore, it has been shown that tyrosine kinase inhibitors synergize with antibodies to EGFR to inhibit the growth of aquamous cell carcinoma in vivo. Thus, a specific erbB-2 kinase inhibitor may also have synergistic effects with Herceptin in the treatment of breast cancer.

The development of small molecule kinase inhibitors of the EGFR family of receptors tyrosine kinases has been so far focused on EGFR itself. Very potent and selective EGFR small molecule kinase inhibitors have been reported and some EGFR small molecule kinase inhibitors have advanced to phase I/II clinical trials for the treatment of certain cancer forms. To date, very few kinase inhibitors selective for erbB-2 were reported.

Therefore, it would be greatly beneficial if new therapies could be designed based on identified existing compounds, rationally modified compounds and/or de novo designed compounds which are active as erbB-2 kinase inhibitors. In particular, it would be helpful if therapies based on compounds having improved selectivity, solubility and stability could be obtained.

SUMMARY AND OBJECTS OF THE INVENTION

It is an object of the invention to provide novel therapies based on inhibiting in vivo the erbB-2 kinase signaling pathway.

It is a more specific object of the invention to provide novel therapies that result in the inhibition of cell proliferation and/or differentiation and/or the promotion of cell apoptosis comprising the administration of a compound that erbB-2 kinase related cell growth signaling.

It is an even more specific object of the invention to provide novel therapies that result in the inhibition of cell proliferation and/or differentiation and/or promotion of cell apoptosis by the administration of a compound having formulae (I) to (V):

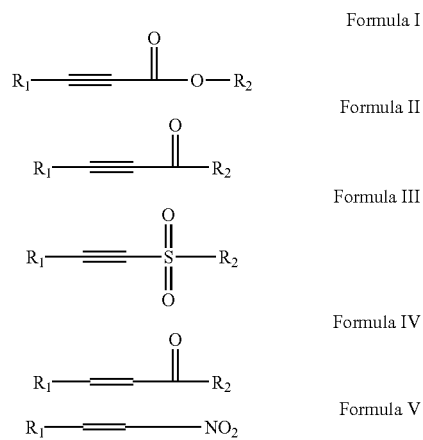

In a preferred embodiment, such therapies will comprise treatment of cancer and other neoplastic conditions.

BRIEF DESCRIPTION OF THE DRAWINGS

FIGS. 1 through 8 illustrate some of the compounds of the invention, methods for identifying those compounds and results of in vitro and in vivo biological test demonstrating the activity of illustrative compounds according to the invention.

DETAILED DESCRIPTION OF THE INVENTION

In cells transformed By erbB-2 overexpression, therapeutic agents inhibiting erbB-2 kinase activity can interrupt the flow of signal transduction mediated by erbB-2 receptor to the ras pathway and may result in the reversal of the cancer phenotype. Thus, one object of the invention is to provide therapies based on inhibition erbB-2 kinase activity.

The present invention provides therapies based on compounds capable of interfering with erbB-2 kinase activity. In one aspect, the invention provides therapies based on existing compounds which are identified through computational modeling as inhibitors of erbB-2 kinase activity. In another aspect, the invention provides novel compounds which are designed by rational design modification or existing compounds or de novo to provide high activity and selectivity and therapies based on these compounds.

In a first aspect, the present invention provides novel therapies based on existing compounds which are identified as potent and selective small molecule inhibitors of erbB-2 kinase. The compounds are identified through structure-based three-dimensional (3D) database searching. The compounds identified through database searching are processed through biological tests to identify one or more lead compounds for clinical testing and/or rational drug design refinement.

Computationally predicting a compound's binding affinity to a host protein involves utilizing the three dimensional (3-D) structures of the host protein and the compound. The 3-D structure of the compound is obtained from a database of chemical compounds. The 3-D structure of the host protein can also be obtained from a protein database.

The invention provides potent and erbB-2 specific kinase inhibitors through a structure-based drug discovery approach.

Figure 1:
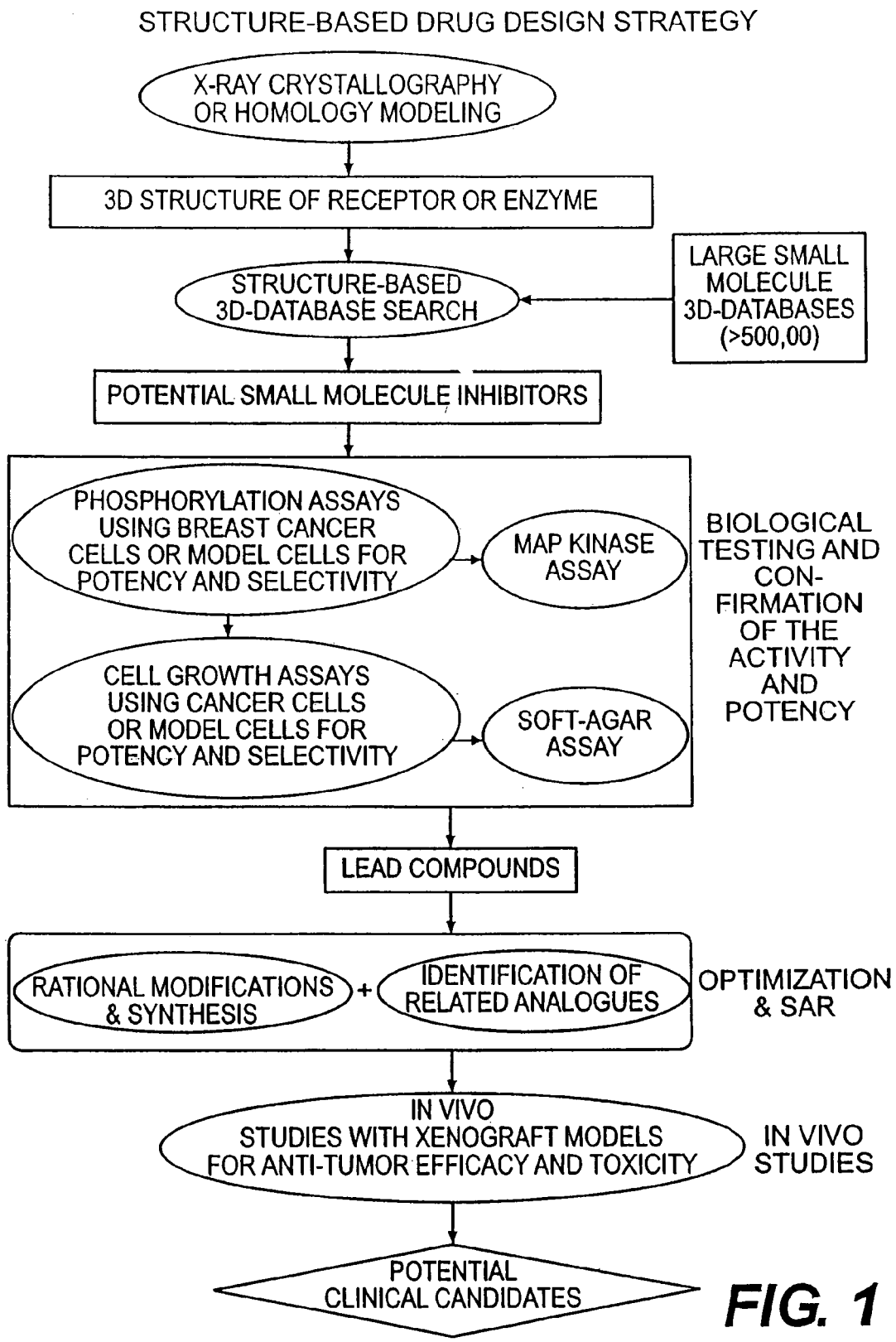

The methodology employed in the discovery of erbB-2 kinase inhibitors is disclosed in U.S. patent application Ser. No. 09/301,339, filed on Apr. 29, 1999, the contents of which are hereby incorporated by reference in their entirety. A flow chart for the methodology is shown in FIG. 1.

Briefly, in structure-based 3D-database searching for drug discovery, once the 3D structure of the target molecule (a receptor or an enzyme) is determined, large chemical databases containing the 3D structures of hundreds of thousands of structurally diverse synthetic compounds and natural products are searched through computerized molecular docking to identify small molecules that can interact effectively with the target or host molecule. In spite of the massive increase in the number of biological molecules whose 3-D structure has been elucidated, the majority of proteins of known primary structure (amino acid sequence) do not have a known tertiary (or 3-D) structure.

For drug design involving target proteins of unknown tertiary structure, a model structure can be constructed based on the known tertiary structure of a protein which is homologous to the target protein. The structure of the homologous protein is used to construct a template structure of all or part of the target protein. The structure obtained through homology modeling provides a working structure for further refinement. The working structure for the protein not having a known structure is obtained by refining the template structure.

In forming a template 3-D structure of the host protein, each atom of the backbone of the target protein is assigned a position corresponding to the position of the equivalent backbone atom in the homologous protein. Similarly, each atom of a side chain of the target protein having an equivalent side chain in the homologous protein is assigned the position corresponding to the position of the atom in the equivalent side chain of the homologous protein. The atom positions of a side chain not having an equivalent in the homologous protein are determined by constructing the side chain according to preferred internal coordinates and attaching the side chain to the backbone of the host protein.

The template structure thus obtained is refined by minimizing the internal energy of the template protein. During the refinement, the positions of the atoms of the side chains having no equivalents in the homologous protein are adjusted while keeping the rest of the atoms of the template protein in a fixed position. This allows the atoms of the constructed side chains to adapt their positions to the part of the template structure determined by homology. The full template structure is then minimized (relaxed) by allowing all the atoms to move. Relaxing the template 3-D structure of the protein eliminates unfavorable contacts between the atoms of the protein and reduces the strain in the template 3-D structure.

Based on the refined structure of the target protein, a host-guest complex is formed by disposing a compound from a compound database in a receptor site of the protein. The structure of the host-guest complex is defined by the position occupied by each atom in the complex in a three dimensional referential.

A geometry-fit group is formed by selecting the compounds which can be disposed in the target binding site without significant unfavorable overlap with the atoms of the protein. For each compound in the geometry fit group, a predicted binding affinity to the receptor site of the host protein is determined by minimizing an energy function describing the interactions between the atoms of the compound and those of the protein. The minimization of the energy function is conducted by changing the position of the compound such that a guest-host complex structure corresponding to a minimum of the energy function is obtained. The compounds having the most favorable energy interaction with the atoms of the binding site are identified for optional further processing, for example through display and visual inspection of compound protein complexes to identify the most promising compound candidates.

The displayed complexes are visually examined to form a group of candidate compounds for in vitro testing. For example, the complexes are inspected for visual determination of the quality of docking of the compound into the receptor site of the protein. Visual inspection provides an effective basis for identifying compounds for in vitro testing.

After putative binding compounds have been identified, the ability of such compounds to specifically bind to erbB-2 kinase is confirmed in vitro and/or in vivo.

The potency and selectivity of potential erbB-2 kinase inhibitors is evaluated in vitro with breast cancer cells overexpressing erbB-2 (MDA-453) or EGFR (MDA-468), model cells (32D cells transfected with EGFR or erbB-2/erbB3, erbB-2/erbB-4, erbB-4), or NIH3T3 cells transfected with EGFR, EGFR/erbB-2 or erbB-2). Potent and selective inhibitors are tested further in their ability to inhibit colony-formation in soft-agarose. Compounds having good in vitro activity are tested in vitro. Tumor bearing mice are treated with therapy, based on the compounds and the effect on the tumor size is observed. Compounds showing effective tumor reduction are then used in clinical trial protocols.

Computational Identification of Compounds Having Potential erbB-2 Kinase Inhibitory Activity To date, the experimental 3D structure (including the kinase domain) of either erbB-2 or EGFR has not been determined. However, the structures of the kinase domain of a number of other receptor tyrosine kinases have been determined through X-ray crystallography. The kinase domain of these receptor tyrosine kinases is closely related to those of erbB-2 and EGFR, which provides an opportunity to model the 3D structure of the kinase domain of erbB-2 and EGFR using the homology modeling approach described above.

Protein kinases, including erbB-2 and EGFR, have an active and an inactive conformation. Inhibition of either of these two conformational states can lead to the inhibition of kinase activity.

The sequences (or primary structures) of erbB-2 and EGFR were obtained from the Protein Gene Bank. Templates for homology modeling were obtained by searching the Protein Databank. 3D structures of the receptors were built using the homology-modeling based on the X-ray structure of the active and inactive insulin receptor tyrosine kinase as a template to model the active and inactive conformation of the erbB-2 and EGFR kinase domains, respectively.

Insulin receptor tyrosine kinase domain has 35% identities, 52% similarities and 10% gaps when compared to that of erbB-2, and 35% identities, 52% similarities and 5% gaps when compared to that of EGFR.

In forming a template structure of the erbB-2 kinase receptor domain, each atom in the backbone of the erbB-2 kinase domain was assigned a position corresponding to the position of the equivalent atom in the 3-D structure of the insulin receptor kinase domain. Similarly, each atom of a side chain of the erbB-2 kinase domain having an equivalent side chain in the insulin receptor kinase domain was assigned a position corresponding to the position of the atom in the equivalent side chain of the insulin receptor kinase domain. The atoms of the side chains of the erbB-2 kinase domain not having equivalents in the insulin receptor kinase domain were determined by positioning the side chain according to its position in the amino acid sequence of ErbB-2 kinase and refining the template structure thus obtained. The refined template structure was then relaxed to reduce the strains which may have been present in the refined template.

Figure 2A:
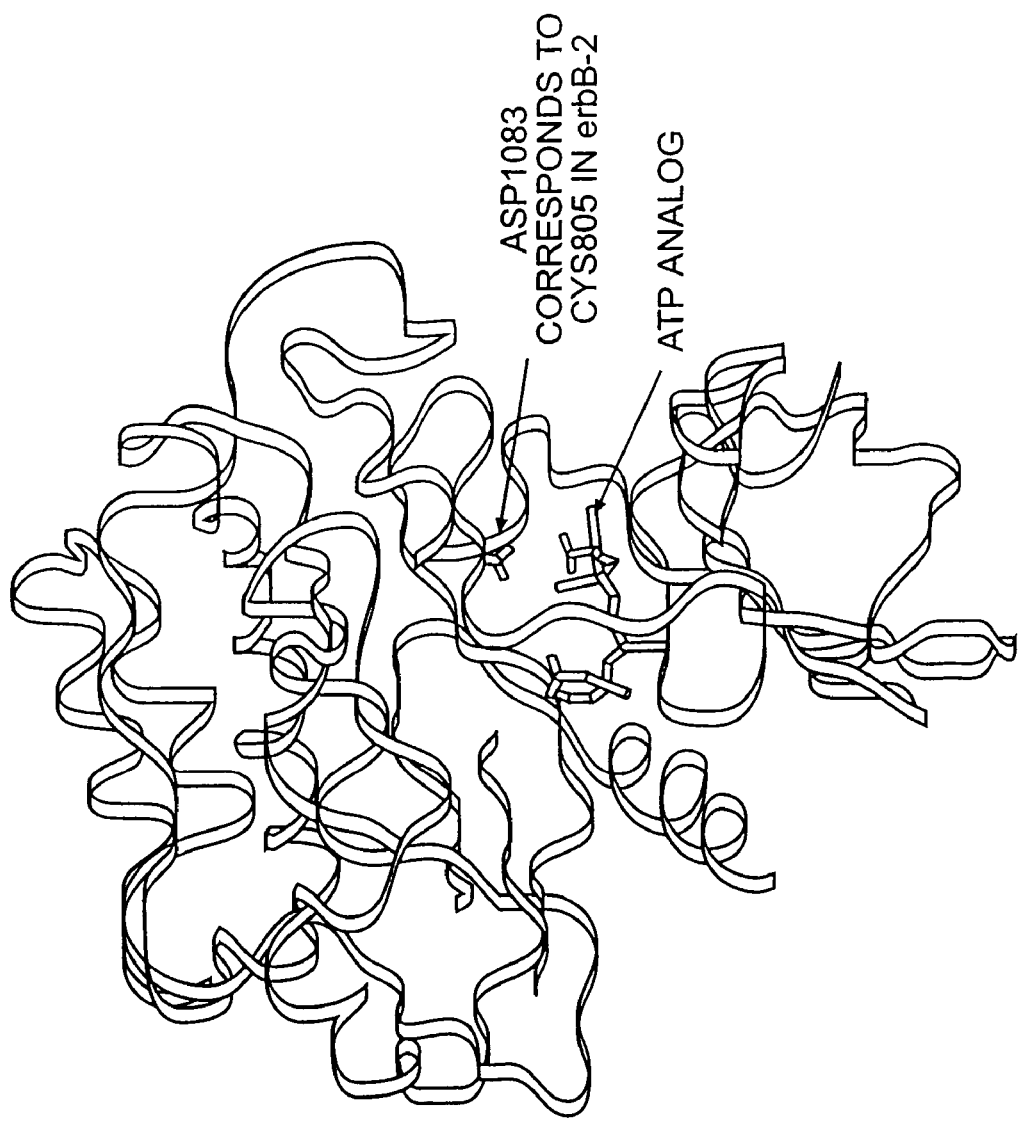
Figure 2B:
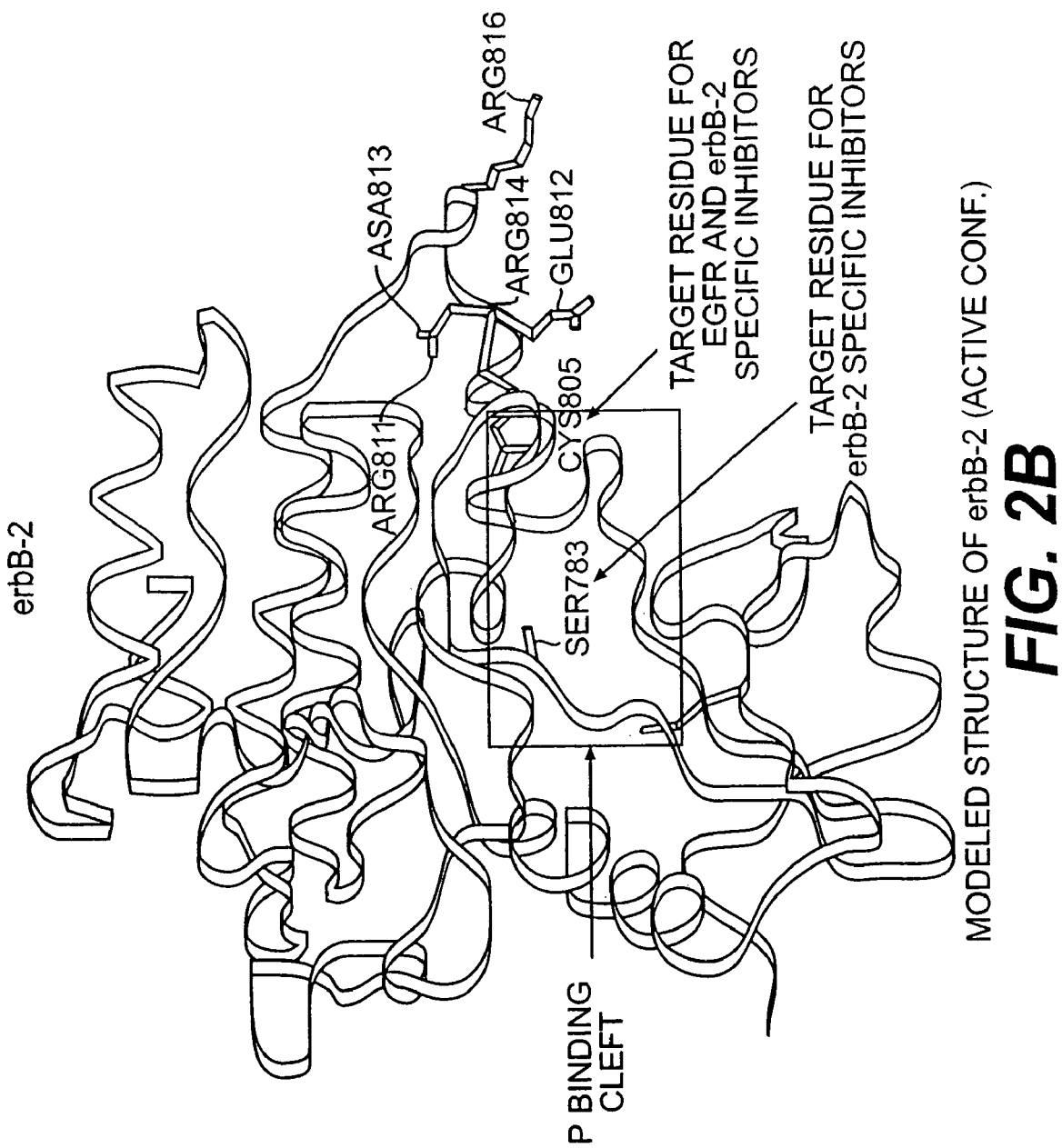

The backbone-3D structures of the activated insulin receptor tyrosine kinase domain and the corresponding model structures of erbB-2 and EGFR are shown in FIG. 2.

The ATP binding site of the erbB-2 kinase domain from the refined structure (both the active and inactive conformation) was used as the target for structure-based database searching.

Database searching was conducted by processing two databases, the National Cancer Institute 3D-database (279,000 compounds) and the Available Chemical Database (250,000 compounds). Each compound in the databases was processed to identify compounds having a shape which is complementary to the shape of the erbB-2 ATP binding site. For each compound, a rigid body docking minimum energy was evaluated and the compounds were ranked according to their rigid body docking energy. In this procedure each compound was rigidly docked into the modeled erbB-2 ATP active site. That is, the compound was docked into the active site without changing the internal coordinates of the compound.

A geometry fit/rigid body docking group was formed by the top 20,000 compounds obtained through shape complementarity ranking. These compounds were further processed by evaluating their energetic binding affinity the ATP binding site of erbB-2 kinase. The compounds were processed through flexible docking processing. That is, the compounds were allowed to adjust their internal coordinates during docking thereby allowing for flexible docking. Flexible docking allowed a more accurate determination of the energy of interaction between each compound and the atoms forming the ATP active site.

The top 2,000 compounds according to the flexible docking energy ranking were further examined to eliminate highly charged compounds whose ability to enter the cell would be greatly hampered by their change. Of the 2000 compounds selected through flexible docking, 1000 compounds were selected for biological processing through in vitro and in vivo testing based on their net electrostatic change.

The potency and selectivity of potential erbB-2 kinase inhibitors was evaluated in vitro with breast cancer cells overexpressing erbB-2 (MDA-453) or EGFR (MDA-468) and model cells (32D cells transfected with EGFR or erbB-2/erbB3, erbB-2/erbB-4, erbB-4, or NIH3T3 cells transfected with EGFR, EGFR/erbB-2 or erbB-2).

The compounds were also tested for inhibitory activities in phosphorylation, cell growth and MAP kinase. Selected compounds were further tested for their ability to inhibit colony-formation in soft-agarose.

Cell proliferation assays were also performed. A soluble tetrazolium/formazan (XTT) assay was performed to directly measure the cell killing activity in a 96-well plate. The soft-agar colony formation assay was employed to directly measure the transforming ability of select compounds as this test provides data that has been shown to correlate well with in vivo tumorigenicity.

In order to show the presence of erbB receptors in the biological materials used in testing the compounds identified or designed according to the invention, a series of antibodies specific for each of the erbB receptors were tested for both western blotting and immunoprecipitation experiments. Those antibodies were utilized to screen the expression of erbB receptors by western blot analysis in various breast cell fines as well as others that over express the erbB receptors. Each receptor was detected with a specific antibody, e.g., EGFR was detected with mAb (UBI), erbB-2 was detected with mAb (Oncogene Sciences), erbB-3 was detected with mAb (Oncogene Sciences), and antiphosphotyrosine mAb (UBI) and visualized with ECL (Amersham). The results for these probing tests are summarized in Table I:

TABLE I

| Cell Line | Origin of Cells | EGFR | erbB-2 | erbB-3 | erbB-4 | Autophos-phorylation at $p^{185}$ or $p^{170}$ | Tumori-genicity |
|---|---|---|---|---|---|---|---|
| MDA-453 | breast | – | +++ | ++ | +++ | +++ | +/– |
| SKBr3 | breast | + | ++++ | ++ | +/– | +++ | |
| BT-474 | breast | +/– | ++++ | +++ | +++ | ++++ | +(E2) |
| NMA-361 | breast | – | +++ | ++ | ++ | +++ | +(E2) |
| MDA-468 | breast | ++++ | – | + | n.d. | +++ | + |
| MDA-231 | breast | ++ | +/– | – | – | + | ++++ |
| A431 | epidermal | +++++ | + | ++ | +/– | ++++ | ++++ |
| MDA-435 | breast. | n.d. | – | ++ | – | – | ++++ |
| MCF-7 | breast | +/– | + | ++ | + | – | +(E2) |
| N87 | gastric | – | +++++ | +++ | ++++ | +++ | +++ |
| SKOV3 | ovarian | – | +++++ | +/– | – | ++ | +++ |

Figure 3:
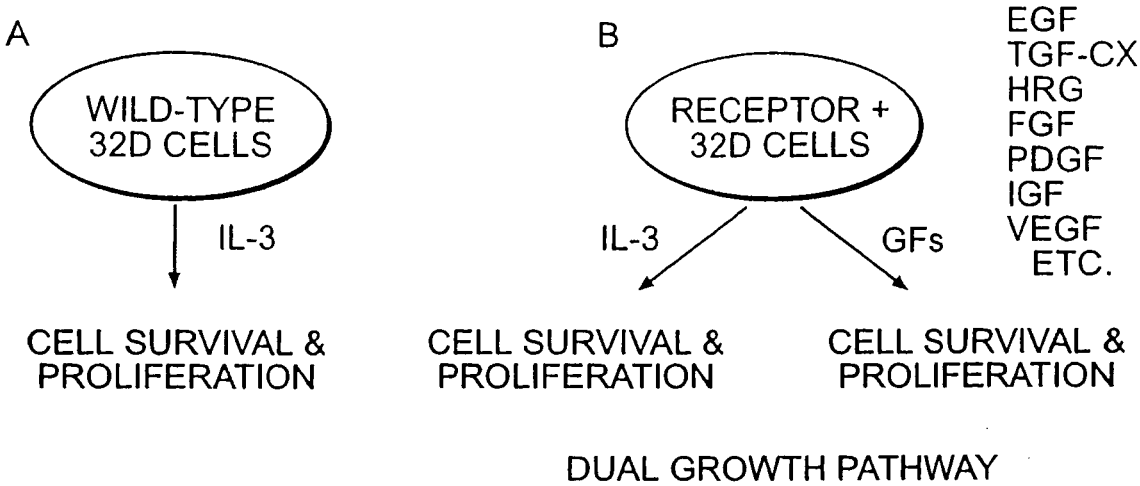
Figure 3:
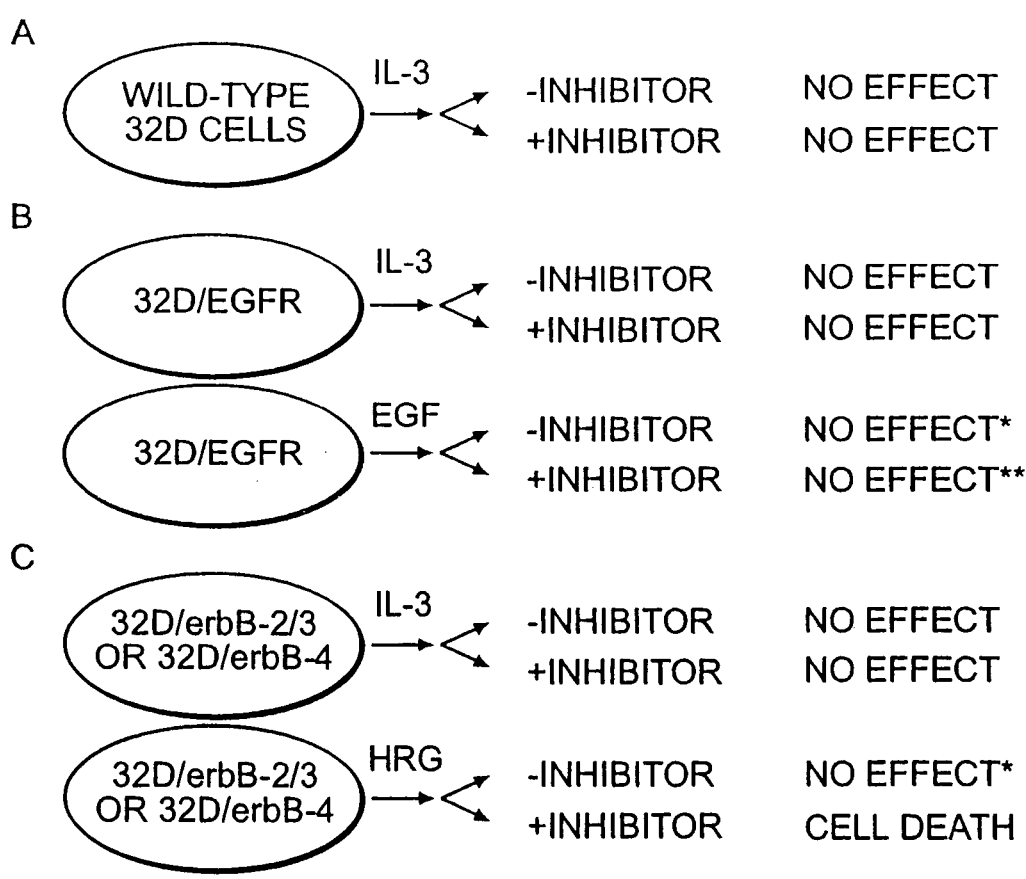

FIG. 3 illustrates in vitro testing using 32D model cells. There are two main advantages of the 32D model cell system. First, the 32D cells are devoid of many receptors, therefore, they provide almost zero background of receptor autophosphorylation or cross-talks between receptors. 32D cells from non-tumorigenic, murine hematopoietic cell lines are devoid of receptors for many growth factors (e.g., EGF, PDGF, erbB-2/3l4. KGF, IL-2, CSF-1, Met, Kit, etc.). Second, when 32D cells are transfected with a particular growth factor receptor, dual niitogenic and signal transduction pathways are created for the same transfectants expressing that receptor. For instance, 32D cells transfected with erbB-4 will proliferate in the presence of either HRG or IL-3. This IL-3 dependence, however, can be bypassed by the stimulation of signal transduction pathways initiated by the expression of specific growth factor receptors and the addition of the appropriate ligand to the culture medium.

In investigating ligand-induced phosphorylation of the erbB-2 receptor, we employed the 32D cells transfected with a combination of erbB-2 and erbB-3, since there is no binding or activation of erbB-2 in single erbB-2 transfected 32D cells. In addition, the NIH 3T3 cells transfected with the chimeric EGFR/erbB-2 receptor were used to test ligand-induced erbB-2 phosphorylation. To investigate ligand-induced phosphorylation of the EGFR receptor, 32D and NIH3T3 cells transfected with EGFR were used.

To investigate the inhibition of autophosphorylation of the erbB-2 receptor kinase, 32D and NIH 3T3 cells transfected with mutant erbB-2, the neu oncogenes, which exhibit a high level of autophosphorylation as employed.

Furthermore, using 32D cells transfected with a single (EGFR, mutant erbB-2, erbB-4) or double receptors (EGFR/erbB-2, erbB-2/erbB-3, erbB-2/erbB-4, EGFR/erbB-3, EGFR/erbB-4), allowed for the determination of preferential inhibitory activity blocking the kinase activity associated with either the homodimers or the heterodimers. NIH3T3 and MCF-7 transfected with other receptor tyrosine kinases including FGFR, PDGFR, VEGFR or ras were employed to evaluate their selectivity over receptor kinases not related with the EGFR family.

141 of the compounds identified through computational processing were tested for their ability to inhibit phosphorylation in human breast cancer cell line MDA-453 that overexpresses erbB-2 obtained by gene amplification. Ten compounds were found to inhibit >90% of the auto-phosphorylation activity of erbB-2 at 100_M. The ten compounds were further tested in a dose-dependent phosphorylation assay both in an MDA-453 cell line, and an MDA-468 cell line. The latter overexpresses the EGFR receptor.

Figure 4B:
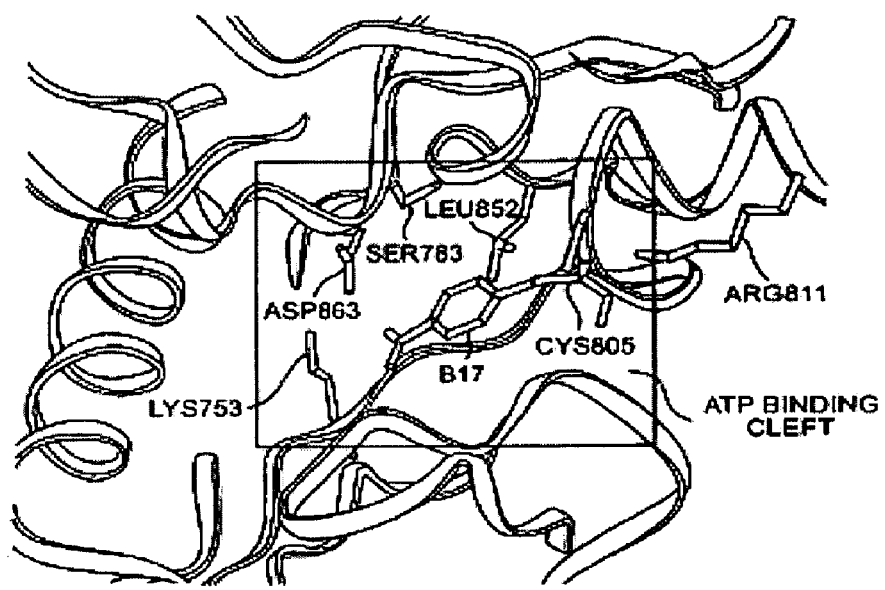
Figure 4A:
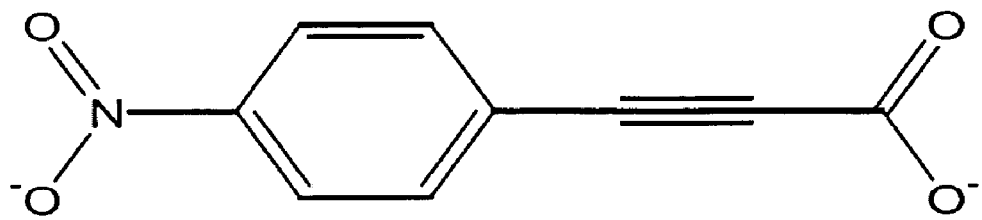

Of the ten compounds identified above, six compounds were found to have relative selectivity in inhibiting phosphorylation in MDA-453 cells over MDA-468 cells. One particular compound that was found to have excellent biological activity is B17. FIG. 4(A) shows the structure of compound B17 and FIG. 4(B) shows compound B17 within the modeled active site of erbB-2 kinase.

FIG. 5(C) shows the irreversible inhibition obtained, by treating the cells with compound B17 for 30 min and washout for 8 hours, then assaying for tyrosine phospohrylation. As shown in FIGS. 5(A) to 5(C), lead compound B17 has excellent potency ($IC_{50}$ was estimated to be approximately 1-2_M) and does not inhibit the EGFR phosphorylation in up to 400_M. The results shown in FIG. 5(A) to 5(C) show, unexpectedly that lead compound B17 has a selectivity more than 100-fold for erbB-2 over EGFR.

B17 exposure did not affect the expression of erbB-2 or EGFR. Moreover, using P32 labeled ATP binding assay, we confirmed that B17 blocks the binding of ATP to erbB-2 but not to EGFR, suggesting that B17 is indeed an ATP competitive inhibitor.

Figure 6:
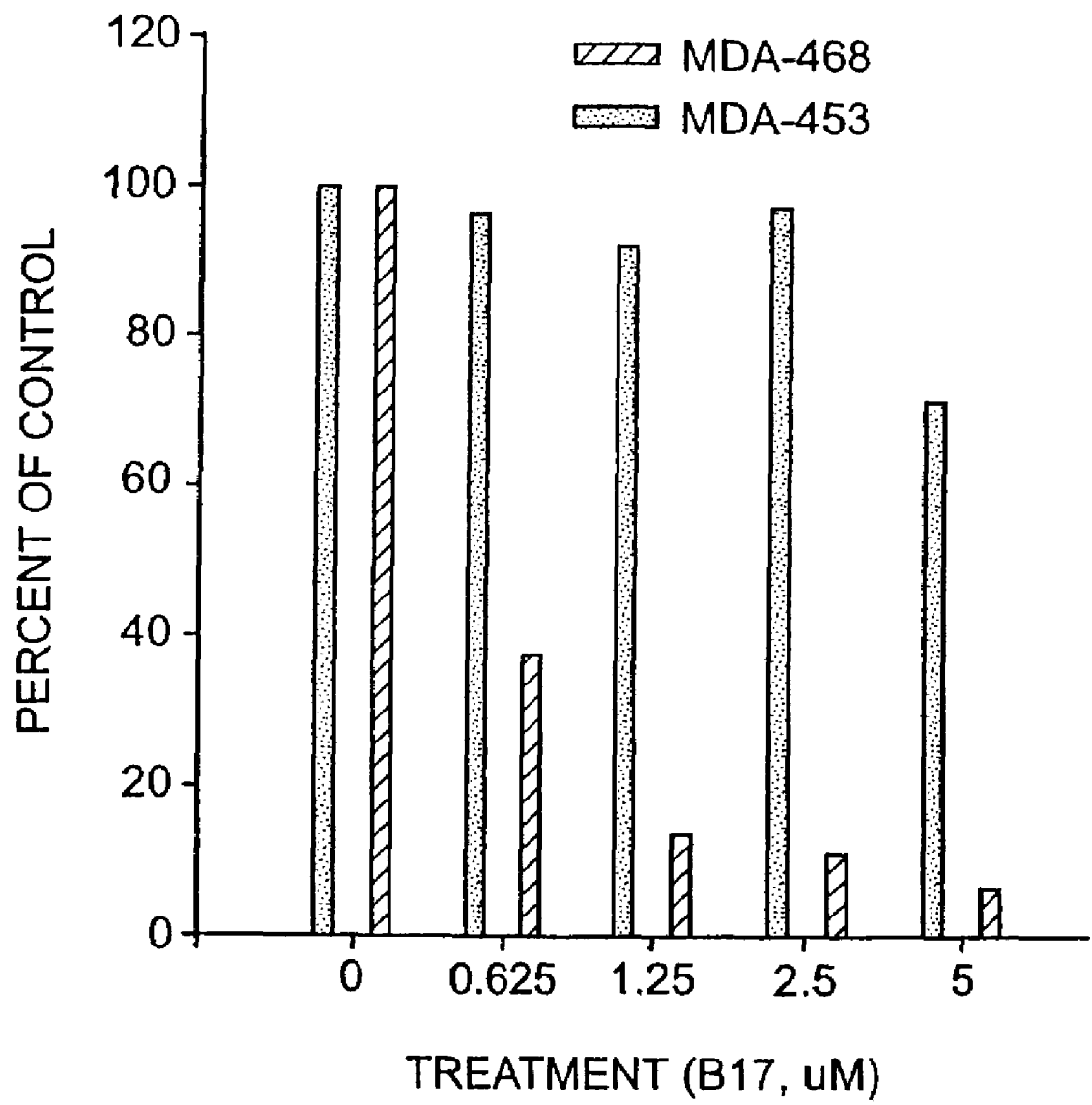

In further probing the biological activity of B17, the NIH-3T3 cells that overexpress either EGFR, erbB-2 or-the chimeric EGFR (extracellular) and erbB-2 (intracellular) receptor through transfection were exposed to treatmetn with B17. Both EGFR and chimeric EGFR/erbB-2 depend on the addition of EGF to induce phosphorylation. Overexpression of erbB-2 receptor resulted in a high level of auto-phosphorylation in these cells. As shown in FIG. 6, lead compound B17 selectively inhibits the EGF-induced erbB-2 kinase activity in the EGFR/erbB-2 chimeric receptor of 3T3-EGFR/erbB-2 cells, but not the EGFR kinase activity in 3T3-EGFR cells. B17 also inhibits the autophosphorylation of erbB-2 in 3T3/erbB-2 cells.

To test if B17 blocks the MAP kinase activity mediated by erbB-2, we tested the MAP linase activity induced by Heregulin in MDA-453 and induced by EGF in MDA-468. We found that the MAP kinase activity in MDA-453 was inhibited by B17 with a potency similar to the inhibition of phosphorylation of erbB-2, while the MAP kinase activity in MDA-468 was not inhibited with concentrations of up to 400_M, indicating that B17 specifically inhibits the erbB-2 receptor mediated MAP kinase signaling pathway.

Figure 7A:
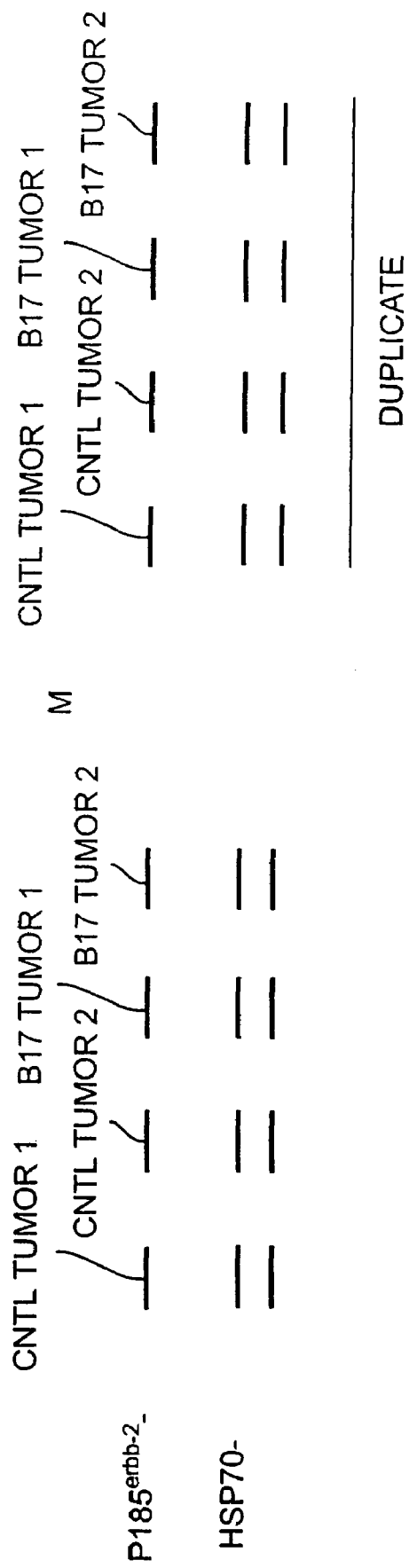
Figure 7B:
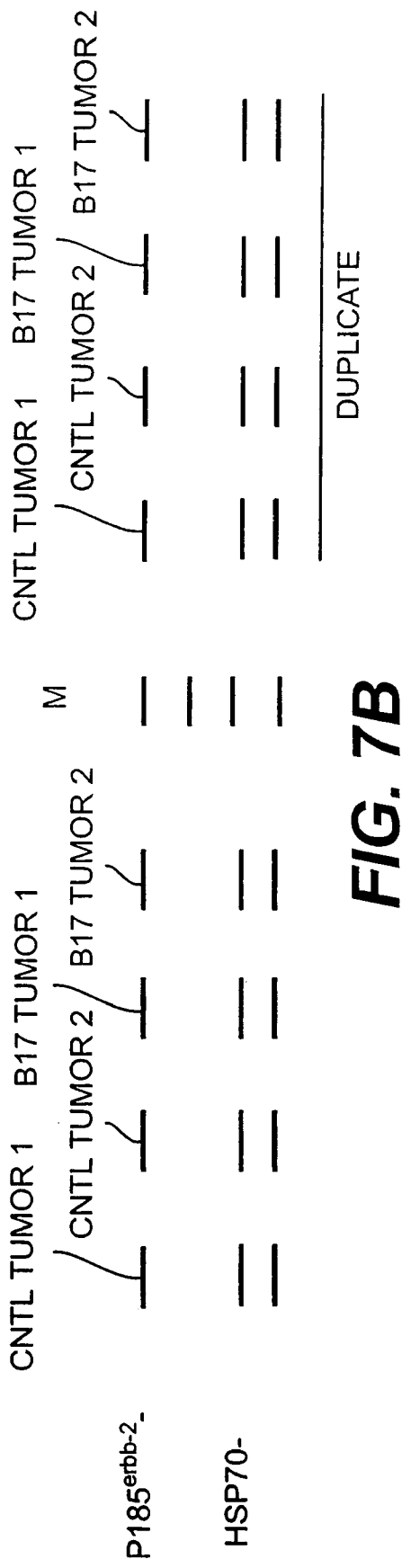
Figure 7C:
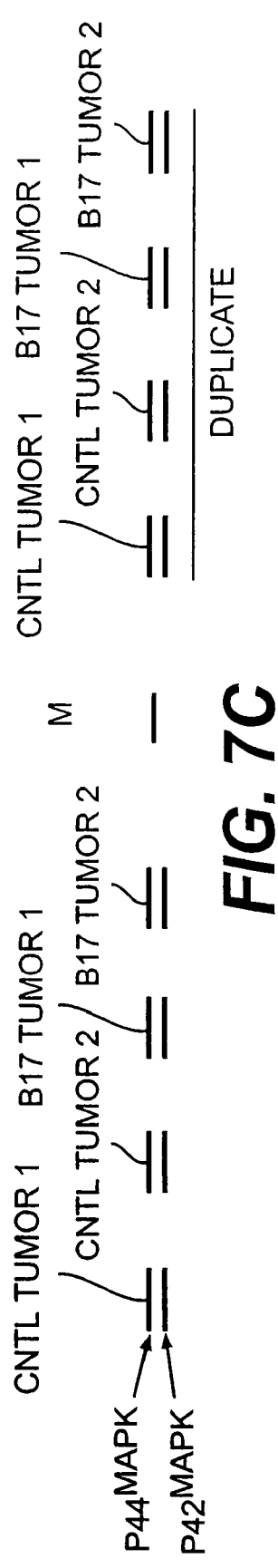
Figure 8:
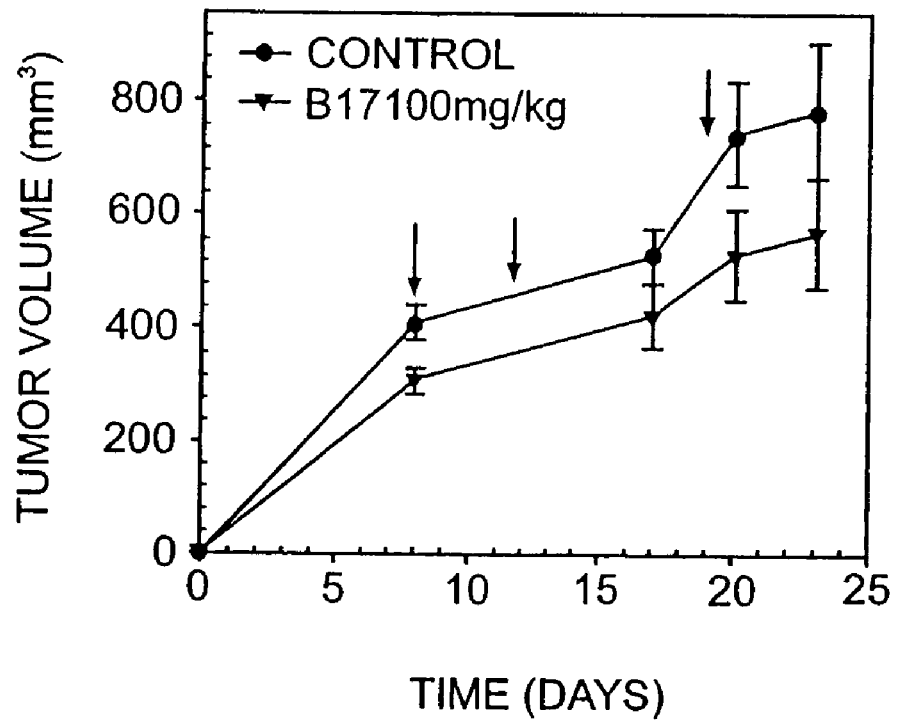

Furthermore, we tested the ability of B17 to inhibit cell growth using MDA-453, 3T3/erbB-2. MDA-468 and 3T3/EGFR. As shown in FIG. 7, it was found that B17 exhibits an $IC_{50} \leq 0.625$_M in MDA-453 and (3T3/erbB-2 data not shown), while only having 25% inhibition at 5_M in MDA-468 (FIG. 4) as shown in FIG. 8 and in NIH3T3/EGFR (data not shown).

FIG. 7 shows the in vivo inhibition of erbB-2 tyrosine phosphorylation in BT-474 cells, which also overexpress the erbB-2 as in MDA-453 cells, but are highly tumorigenic in nude mice. The figure shows that in tumor-bearing mice (BT-474), there is more than 70% (⅔) reduction in erbB-2 phosphorylation activity compared with the activity obtained for control untreated tumors. The activity of the B17 compound in animal systems was further probed. FIG. 8 shows that down-stream effector protein, MAP kinase phosphorylation is markedly reduced by in vivo treatment of B17 in tumor cells. As shown in FIG. 8, no change in the expression level of Cerb -2 protein was observed in human breast carcinoma BT-974 cells 24 hours after intraperitonial injection 100 mg/kg of B17.

Longterm in vivo efficacy investigations were conducted on mice treated with 100 mg/kg of B17, by intraperitonial injection twice per week. As shown in FIG. 9, the treatment produced about 28% reduction of tumor volume compared to controls at day 15.

The above results indicate that lead compound B17 is a fairly potent ATP competitive kinase inhibitor which selectively blocks the erbB-2 kinase activity, thereby shutting-down erbB-2 mediated signaling transduction pathway. When added directly to cells in culture, it was found that B17 inhibits cellular proliferation of erbB-2 overexpressing cells. In addition, we found that B17 is an irreversible inhibitor.

Based on the unexpected biological activity and selectivity found for the compound B17, the compound databases were further searched to identify analogs of B17 that may have even greater activity and/or selectivity in inhibiting erbB-2 activity. The search in the NCI database produced over 40 closely related analogues of lead compound B17.

The following is a table showing the chemical structure and activity of some of the analogues of B17:

Rotational Drug Design of erbB-2 Kinase Inhibitors

In another aspect, the present invention provides novel compounds which are rationally designed to inhibit erbB-2 kinase activity. Rational design of the novel compounds is based on information relating to the binding site of the erbB-2 kinase protein. The structures of the protein and a lead compound is analyzed such that compound structures having possible activity in binding to the binding site are formulated.

The structure of the lead compounds is divided into design blocks the modification of which is probed for influence on the interactions between the lead compound and the active site. Compounds having different design block combinations are then synthesized and their activity in relation to the identified mechanism is tested. Such tests are conducted in vitro and/or in vivo, in the same manner described above for lead compound B17. The information obtained through such tests is then incorporated in a new cycle of rational drug design. The design-synthesis-testing cycle is repeated until a lead compound having the desired properties is identified. The lead compound is then clinically tested.

As discussed above in connection with the modeling of the structure of the erbB-2 kinase domains, it has been found that erbB-2 and EGFR have a very similar ATP binding site as compared to other receptor kinases such as insulin receptor tyrosine kinase. However, the erbB-2 kinase domain has two distinctive residues (Cys805 and Ser753) located at the ends of the ATP binding site (FIG. 1). The Cys805 is common within the EGFR family but not shared by other receptor kinases. Ser783 is unique to erbB-2 (EGFR has a Cys residue at this position).

The distinguishing structural features of the erbB2 receptor site were employed as a guide in rationally designing novel compounds having enhanced binding activity and selectivity towards the erbB-2 receptor. The structure of lead compound B17 was rationally modified to enhance the interactions between B17 and the Ser 780.

Based on the above computational modeling, database searching, rational drug design, in vitro and in vivo biological testing, the present inventors have discovered that compounds having the generic formula set forth below specifically interact with erbB-2 kinase molecules:

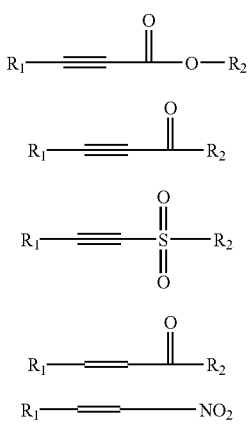

Thus, the compounds produced according to the invention will be used to treat conditions wherein inhibition of erbB-2 kinase signaling is therapeutically beneficial. This will include conditions that involve abnormal cell growth and/or differentiation such as cancers and other neoplastic conditions. Also, the subject compounds may be used to treat other conditions involving abnormal cell proliferation and/or differentiation such as dermatological conditions and disorders. Also, the subject compounds may be useful in treating inflammatory conditions such as arthritis, psoriasis, autoimmune disorders such as myasthenia gravis, lupus, multiple sclerosis, and others, and conditions involving abnormal platelet aggregation. The preferred indication is cancer, especially cancers involving over-expression of erbB-2 EGF and/or the PDGF receptor, cancers that express mutant ras, or cancers which comprise a Bcr/Abl translocation. Examples of cancers which may be treated according to the invention include breast colon, pancreatic, prostate, head and neck, gastric, renal, brain and CML.

The subject therapies will comprise administration of at least one compound according to the invention in an amount sufficient to elicit a therapeutic response, e.g., inhibition of tumor cell proliferation and/or differentiation and/or promotion of apoptosis.

The compound may be administered by any pharmaceutically acceptable means, by either systemic or local administration. Suitable modes of administration include oral, dermal, e.g., via transdermal patch, inhalation, via infusion, intranasal, rectal, vaginal, topical parenteral (e.g., via intraperitoneal, intravenous, intramuscular, subcutaneous, injection).

Typically, oral administration or administration via injection is preferred. The subject compounds may be administered in a single dosage or chronically dependent upon the particular disease, condition of patient, toxicity of compound, and whether this compound is being utilized alone or in combination with other therapies. Chronic or repeated administration will likely be preferred based on other chemotherapies.

The subject compounds will be administered in a pharmaceutically acceptable formulation or composition. Examples of such formulations include injectable solutions, tablets, milk, or suspensions, creams, oil-in-water and water-in-oil emulsions, microcapsules and microvesicles.

These compositions will comprise conventional pharmaceutical excipients and carriers typically used in drug formulations, e.g., water, saline solutions, such as phosphate buffered saline, buffers, surfactants.

The subject compounds may be free or entrapped in microcapsules, in colloidal drug delivery systems such as liposomes, microemulsions, and macroemulsions. Suitable materials and methods for preparing pharmaceutical formulations are disclosed in *Remington's Pharmaceutical Chemistry*, 16 Edition, (1980). Also, solid formulations containing the subject compounds, such as tablets, and capsule formulations, may be prepared.

Suitable examples thereof include semipermeable materials of solid hydrophobic polymers containing the subject compound which may be in the form of shaped articles, e.g., films or microcapsules, as well as various other polymers and copolymers known in the art.

The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight.

The subjects treated will typically comprise mammals and most preferably will be human subjects, e.g., human cancer subjects.

The compounds of the invention may be used alone or in combination. Additionally, the treated compounds may be utilized with other types of treatments, e.g., cancer treatments. For example, the subject compounds may be used with other chemotherapies, e.g., tamoxifen, taxol, methothrexate, biologicals, such as antibodies, growth factors, lymphokines, or radiation, etc. Combination therapies may result in synergistic results. In particular, the compounds may be advantageously used in conjunction with herceptin based therapies.

The preferred indication is cancer, especially the cancers identified previously While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A compound that inhibits erbB-2 kinase activity through targeting the SER783 residue of an erbB-2 protein, wherein said compound is

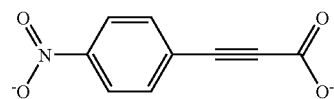

or a pharmaceutically acceptable salt thereof.

2. The composition of claim 1, wherein said composition is able to inhibit cellular proliferation of cells overexpressing erbB-2.

3. A pharmaceutical composition comprising the composition of claim 1, and a herceptin based anti-cancer agent.

* * * * *